(12) United States Patent
Gryczynski et al.

(10) Patent No.: US 7,956,989 B2
(45) Date of Patent: Jun. 7, 2011

(54) SURFACE PLASMON ASSISTED MICROSCOPE

(75) Inventors: Zygmunt Gryczynski, Fort Worth, TX (US); Ignacy Gryczynski, Fort Worth, TX (US); Nils Calander, Gothenburg (SE); Julian Borejdo, Dallas, TX (US)

(73) Assignee: University of North Texas Health Science Center at Fort Worth, Fort Worth, TX (US)

( * ) Notice: Subject to any disclaimer, the term of this patent is extended or adjusted under 35 U.S.C. 154(b) by 384 days.

(21) Appl. No.: 12/018,107

(22) Filed: Jan. 22, 2008

(65) Prior Publication Data

US 2008/0231834 A1    Sep. 25, 2008

Related U.S. Application Data

(60) Provisional application No. 60/881,645, filed on Jan. 22, 2007.

(51) Int. Cl.
*G01N 1/00* (2006.01)
(52) U.S. Cl. .......................................... 356/36
(58) Field of Classification Search ........... 356/445–448
See application file for complete search history.

(56) References Cited

U.S. PATENT DOCUMENTS

| | | | |
|---|---|---|---|
| 6,194,223 B1 * | 2/2001 | Herrmann et al. | 436/518 |
| 6,280,960 B1 * | 8/2001 | Carr | 435/7.2 |
| 7,118,907 B2 | 10/2006 | Williams et al. | |
| 7,298,549 B2 | 11/2007 | Muller | |
| 7,318,907 B2 * | 1/2008 | Stark et al. | 422/50 |
| 7,426,040 B2 * | 9/2008 | Kim et al. | 356/519 |
| 2006/0274314 A1 * | 12/2006 | Thomsen et al. | 356/445 |
| 2009/0079978 A1 * | 3/2009 | Kimura | 356/301 |

OTHER PUBLICATIONS

Borejdo, J., et al., "Application of surface plasmon coupled emission to study of muscle." Biophys J (2006), 91(7):2626-35.
Borejdo, J., et al., "Fluorescence Correlation Spectroscopy in Surface Plasmon Coupled Emission Microscope." Optics Express (2006), 14(17):7878-7888.
Burghardt, T. P., et al., "In Situ Fluorescent Protein Imaging with Metal Film-Enhanced Total Internal Reflection Microscopy," Biophys J (2006), 90:4662-4671.
Calander, N., Theory and simulation of surface plasmon-coupled directional emission from fluorophores at planar structures. Anal Chem (2004), 76(8):2168-73.

(Continued)

*Primary Examiner* — Michael P Stafira
(74) *Attorney, Agent, or Firm* — Chalker Flores, LLP; Edwin S. Flores

(57) ABSTRACT

The present invention includes a microscope and a method for using the microscope for single molecule with reduced photobleaching of a fluorophore (20) that includes a light translucent material (16); a metal layer (18) disposed on the light translucent material (16); a medium (15) disposed on the metal layer (18), the medium (15) having one or more fluorophores (20) capable of binding a target analyte (e.g., inside a cell); a microscope positioned to observe the surface plasmon emissions from the one or more fluorophores (20) within 50 nanometers of the surface of the metal layer (18); an excitation source capable of exciting the one or more fluorophores (20), the excitation source positioned to strike the light translucent material (16) at a first angle; and a light detector (38) that selectively detects emitted light generated by excited fluorophores (20) at a second angle (22), wherein light emitted by the one or more fluorophores (20) at the surface plasmon angle is detected through the microscope, such that single molecules may be detected without significantly degrading fluorophore (20) emissions.

36 Claims, 10 Drawing Sheets

OTHER PUBLICATIONS

Gryczynski, I., et al., "Radiative decay engineering 4. Experimental studies of surface plasmon-coupled directional emission." Anal Biochem (2004), 324(2):170-82.

Gryczynski, I., et al., "Surface plasmon-coupled emission using gold film." J. Phys. Chem. B (2004), 108:12568-12574.

Gryczynski, Z., et al., "Minimization of detection volume by surface-plasmon-coupled emission." Anal Biochem (2006), 356(1):125-31.

Lakowicz, J. R., Radiative decay engineering: biophysical and biomedical applications. Anal Biochem (2001), 298(1):1-24.

Lakowicz, J. R., et al., "Intrinsic fluorescence from DNA can be enhanced by metallic particles." Biochem Biophys Res Commun (2001), 286(5):875-9.

Lakowicz, J. R., et al., "Radiative decay engineering. 2. Effects of Silver Island films on fluorescence intensity, lifetimes, and resonance energy transfer." Anal Biochem (2002), 301(2):261-77.

Lakowicz, J. R., et al., "Directional surface plasmon-coupled emission: A new method for high sensitivity detection." Biochem Biophys Res Commun (2003), 307(3):435-9.

Lakowicz, J. R., Radiative decay engineering 3. Surface plasmon-coupled directional emission. Anal Biochem (2004), 324(2):153-69.

Malicka, J., et al., "Increased resonance energy transfer between fluorophores bound to DNA in proximity to metallic silver particles." Anal Biochem (2003), 315(2):160-9.

Malicka, J., et al., "Use of surface plasmon-coupled emission to measure DNA hybridization." J Biomol Screen (2004), 9(3):208-15.

Malicka, J., et al., "Effects of metallic silver island films on resonance energy transfer between N,N'-(dipropyl)-tetramethyl-indocarbocyanine (Cy3)- and N,N'-(dipropyl)-tetramethyl-indodicarbocyanine (Cy5)-labeled DNA." Biopolymers (2003), 70(4):595-603.

Matveeva, E., et al., "Metal-enhanced fluorescence immunoassays using total internal reflection and silver island-coated surfaces." Anal Biochem (2004), 334(2):303-11.

miRBase::Sequences. http://microma.sanger.ac.uk/cgi-bin/sequences/browse.pl (Jul. 31, 2007).

Muthu, P., et al., "Decreasing photobleaching by silver island films: application to muscle." Anal Biochem (2007), 366(2):228-36.

Neogi, A., et al., "Coupling of spontaneous emission from GaN-AlN quantum dots into silver surface plasmons." Opt Lett (2005), 30(1):93-5.

* cited by examiner

KRETSCHMANN CONFIGURATION

US 7,956,989 B2

SURFACE PLASMON ASSISTED MICROSCOPE

CROSS-REFERENCE TO RELATED APPLICATIONS

This application claims priority to U.S. Provisional Patent Application Ser. No. 60/881,645, filed Jan. 22, 2007, the entire contents of which are incorporated herein by reference.

STATEMENT OF FEDERALLY FUNDED RESEARCH

This invention was made with U.S. Government support under Contract Nos. AR 048622 and CA114460 awarded by the NIH. The government has certain rights in this invention.

TECHNICAL FIELD OF THE INVENTION

The present invention relates in general to the field of microscopy, and more particularly, to microscopes capable of single molecule detection in cells.

BACKGROUND OF THE INVENTION

Without limiting the scope of the invention, its background is described in connection with single molecule imaging.

Currently it is difficult and time consuming to measure the activity of single molecules at specific points in a biochemical pathway within a living cell. Such experiments are extremely important to both drug discovery and basic biological research. There is a large movement in the drug discovery field toward the area of high content cellular screening, which has become a valuable tool for understanding where in a cell a specific drug exerts its effects.

U.S. Pat. No. 7,318,907, issued to Stark, et al., teaches a surface plasmon enhanced illumination system, teaches methods and apparatus for producing small, bright nanometric light sources from apertures that are smaller than the wavelength of the emitted light. Light is directed at a surface layer of metal onto a light barrier structure that includes one or more apertures each of which directs a small spot of light onto a target. The incident light excites surface plasmons (electron density fluctuations) in the top metal surface layer and this energy couples through the apertures to the opposing surface where it is emitted as light from the apertures or from the rims of the apertures. Means are employed to prevent or severely limit the extent to which surface plasmons are induced on the surface at the aperture exit, thereby constraining the resulting emissions to small target areas. The resulting small spot illumination may be used to increase the resolution of microscopes and photolithographic processes, increase the storage capacity and performance of optical data storage systems, and analyze the properties of small objects such as protein and nucleic acid molecules and single cells.

U.S. Pat. No. 7,118,907, issued to Williams, teaches a single molecule detection systems and methods. Briefly, a microfluidic system is provided that includes a substrate, a first microchannel disposed in the substrate for providing a reactant to a reaction zone, a second microchannel disposed in the substrate, and a third microchannel disposed in the substrate, the third microchannel providing fluid communication between the first and second microchannels. The system also typically includes first and second electrodes, positioned at opposite ends of the second microchannel, for providing an electric field within the second microchannel. In operation, when the reactant is in the reaction zone, a reaction product is produced having a net electric charge different from the electric charge of the reactant.

Finally, U.S. Pat. No. 7,298,549, issued to Muller teaches a confocal microscope has a specimen holding device for holding a specimen. The specimen is illuminated by an illuminating unit. An optics unit serves to direct radiation produced by the illuminating unit toward the specimen and to direct the radiation emitted by the specimen toward a detector unit. The confocal microscope also comprises an aperture diaphragm that is placed in the beam path in front of the detector unit. In addition, a focusing lens is provided in the beam path in front of the aperture diaphragm. The focusing lens can be moved in order to adjust the confocal microscope, for example, in order to compensate for thermal stresses.

SUMMARY OF THE INVENTION

The present invention includes an apparatus and method for surface plasmon assisted microscopy, wherein the microscope is capable of detecting single molecules, the microscope system including: a light translucent material; a metal layer disposed on the light translucent material, wherein the thickness of the metal layer is 50 nM or less; a medium disposed on the metal layer, the medium comprising one or more fluorophores capable of binding a target analyte; a microscope positioned to observe the emission from the one or more fluorophores in the medium; an excitation source capable of exciting the one or more fluorophores, the excitation source positioned to strike the light translucent material at a first angle; and a light detector that detects emitted light generated by excited fluorophores at a second angle, wherein light emitted by the one or more fluorophores at the surface plasmon angle is detected through the microscope, such that single molecules may be detected without significantly degrading fluorophore emissions.

In one aspect, the metal layer includes silver, gold, aluminum, or copper. In another aspect, the metal is deposited onto the light translucent material by vapor deposition, electroless plating, chemical vapor deposition, or photoreduction. In one aspect, the light translucent material glass, silica, a polymer, quartz, plastic, borosilicate glass and combinations thereof. In one aspect, the excitation source is arranged to direct light comprising the excitation wavelength through the light translucent material and then to the metal layer such that the angle of incidence on the first layer is equal to the surface plasmon angle of said excitation wavelength. In one aspect, the microscope comprises a high numerical aperture (NA) objective. In one aspect, the target comprises a molecule within a cell. In one aspect, the detector selectively detects light emissions from within a cell. In one aspect, the detection of the one or more fluorophores is from fluorophores that are within 50 nM from the metal surface. In one aspect, the light detector detects light emissions over time and stores the images. In one aspect, the functional molecules either comprise a plurality of types of fluorophores that target one or more different target molecules concurrently.

Another embodiment of the present invention is a surface plasmon assisted microscope system capable of detecting single molecules, the microscope system having: a light translucent material; a metal layer disposed on the light translucent material, wherein the thickness of the metal layer is 50 nM or less; a medium disposed on the metal layer, the medium comprising one or more fluorophores capable of binding a target analyte; an excitation source positioned to traverse a microscope objective before crossing the light translucent material and striking the metal layer, wherein surface plasmons created by the combination of exciting the one or more fluorophores in the sample are amplified at the metal layer, wherein the light strikes the translucent layer at a first angle; a microscope positioned to capture the emission from the one or more fluorophores in the medium at a second angle; and a light detector positioned to selectively detect emitted light generated by excited fluorophores that are amplified the surface plasmons, such that single molecules may be detected.

The present invention also includes a method for detecting fluorescence using surface plasmon-coupled emission with a microscope, by positioning a light translucent material onto which a metal layer capable of surface plasmon amplification has been formed in a light path; binding an analyte to one or more fluorophores in a sample on the metal surface, wherein the fluorophores are within 50 nanometers of the metal surface; striking the analyte and the one or more types of fluorophores with a coherent light at a first angle, wherein the combination of fluorescence emission and the surface plasmons emit light at a second angle; and detecting the light emitted at the second angle, wherein light emitted by the one or more fluorophores at the second angle is detected through the microscope, such that the analyte may be detected without significantly degrading fluorophore emissions. In one aspect of the method, the microscope and the light source are positioned in a Reverse Kretschmann configuration. In another aspect, the microscope and the light source are positioned in a Kretschmann configuration. The analyte may be, for example, at least one of antibodies, fragments of antibodies, peptides, antigens, nucleic acids, polypeptides, lipids, carbohydrates, polysaccharides, minerals, vitamins, cells and tissues. The analyte may even be bound to the one or more fluorophores, e.g., covalently or non-covalently.

Yet another embodiment of the present invention is a method for detecting fluorescence of single molecules using surface plasmon-coupled emission without degrading fluorophore emissions with a microscope, by positioning a light translucent material onto which a metal layer capable of surface plasmon amplification has been formed in a light path; binding an analyte to one or more fluorophores in a sample that is disposed on the metal surface, wherein the fluorophores are within 50 nanometers of the metal surface; striking the analyte and the one or more types of fluorophores with a coherent light at a first angle, wherein the combination of fluorescence emission and the surface plasmons emit light at a second angle and the metal later forms a mirror that reflects non amplified emissions as the second angle that are non-specific or rather than 50 nanometers from the metal surface; and detecting the light emitted at the second angle, wherein light emitted by the one or more fluorophores at the second angle is detected through the microscope, such that the analyte may be detected without significantly degrading fluorophore emissions.

BRIEF DESCRIPTION OF THE DRAWINGS

For a more complete understanding of the features and advantages of the present invention, reference is now made to the detailed description of the invention along with the accompanying figures and in which:

FIG. 2a—Reverse Kretschmann configuration (RK) excitation, Surface Plasmon Coupled Emission (SPCE) observation; FIG. 2b—RK excitation, Free Space (FS) observation; FIG. 2c—Kretschmann configuration (KR) excitation, SPCE observation; d—KR excitation, FS observation.

FIG. 20 (right), is a time course of photobleaching of molecule indicated by the arrow (arrowhead is background which was subtracted from signal). Bar is 10 um.

DETAILED DESCRIPTION OF THE INVENTION

Figure 1:
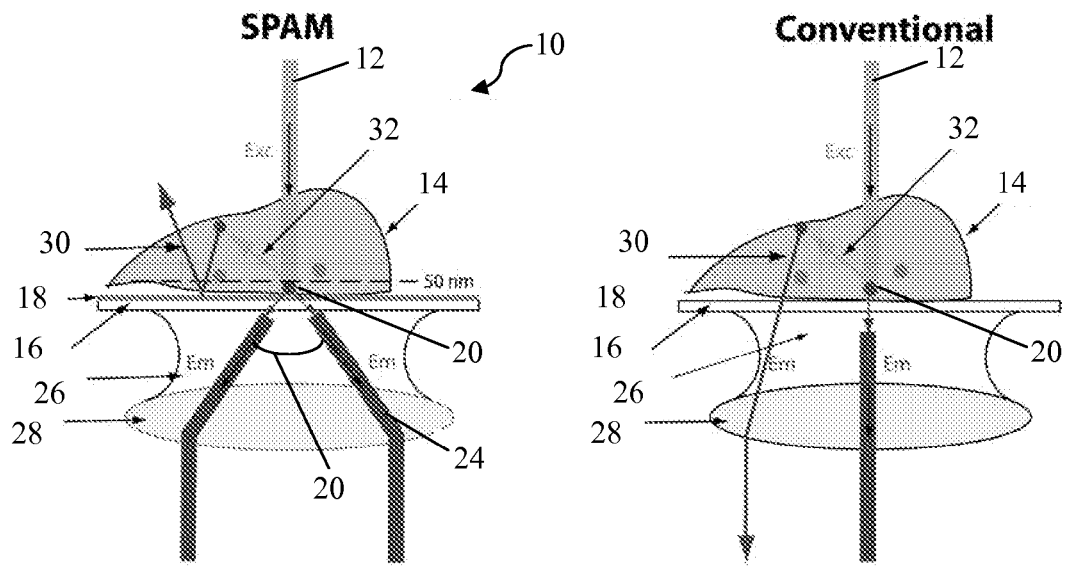
FIG. 1 shows one configuration of a Surface Plasmon Assisted Microscope (SPAM).

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Abbreviations: SPAM—Surface Plasmon Assisted Microscope; SP—Surface Plasmons; TIR—Total Internal Reflection; KR—Kretschmann configuration; RK—Reverse Kretschmann configuration; SPCE—Surface Plasmon Coupled Emission; SMD—Single Molecule Detection; NSOM—Near-Field Scanning Optical Microscopy; SPR—Surface Plasmon Resonance; ROI—Region-of-Interest; AFM—Atomic Force Microscope; TIRF—Total Internal Reflection Fluorescence; RhB—rhodamine B; DCM—4-(Dicyanomethylene)-2-methyl-6-(p-dimethylaminostyryl) 4H-pyran.

The Surface Plasmon Assisted Microscope (SPAM) of the present invention was used to image single molecules in living cells. Imaging single molecules allows the investigator to measure enzymatic chemistry or mechanics without averaging that is inherent in studying large assemblies. The study of single molecules enables characterization of the heterogeneity that is intrinsic to an individual molecule at different parts of a biological pathway. SPAM allows measurements in intact cells where proteins exist in their native (crowded) environment.

SPAM microscope. SPAM microscopes may be used to observe sample illuminated by collimated laser beam from above (Reverse Kretchmann) or below (Kretchmann) configuration. The fluorescence in cells is excited by Surface Plasmons (SP) propagating in a thin layer of noble metal coating the surface of a coverslip. Fluorescence is emitted only at high angles and is collected by high numerical aperture objective. The final version of SPAM will incorporate a condenser to fill the entrance aperture of the objective, a Calcite Beam Splitter to give it the ability to measure rotational motions, a simplified version of a total internal reflection (TIR) exciter to illuminate samples from below (Kretchmann configuration), and will use an Optovar to avoid undersampling.

SPAM versus TIRF microscope. The standard against which the performance of SPAM will be tested is TIRF microscope—the method of choice to detect single molecules. Five key parameters will be compared: (i) background rejection, (ii) thickness of optical section, (iii) photobleaching, (iv) effect on optical resolution, and (v) ability to image single molecules. The SPAM microscope will be considered feasible if the background rejection is 10 times better, optical section is <50 nm thick, resolution is equal to the diffraction limit, and single molecules can be visualized.

Single molecule imaging in a cell. After making sure that the criteria specified above are met, the SPAM can be applied to detect single molecule in a cell. Skeletal muscle myofibrils will be used as a test sample. Myofibrils are convenient test sample because they are alive (in a sense that addition of ATP induces shortening) and contain sub-micron structures well suited to measure optical resolution. The detection of single molecules can be verified by observing step-wise photobleaching.

Currently it is difficult and time consuming to measure the activity of single molecules at specific points in a biochemical pathway within a living cell. Such experiments are extremely important to both drug discovery and basic biological research. There is a large movement in the drug discovery field toward the area of high content cellular screening, which has become a valuable tool for understanding where in a cell a specific drug exerts its effects. The main advantages of SPAM over its competitor, TIRF, are 10-fold better background rejection, no effect on optical resolution, less than 50 nm thickness of optical section and the ability to image single molecules in vitro and in vivo.

The chief technique used to image single molecules has been TIRF microscope, because of its good background rejection, thin optical sectioning and good optical resolution. While other techniques exist, they are expensive and time consuming. In addition to exceeding performance of TIRF in all these areas, the SPAM microscope opens up the field of single molecule imaging to most laboratories by making the instrument affordable and technically simple to use. With the advent of the SPAM technique, it is estimated by some that the size of the field will increase rapidly.

Using the present invention it was found that the SPAM microscope delivered superior background suppression in the bulk with enhanced single molecule, in-context detection, that allowed signal collection from exceedingly thin section of samples. It was also found that SPAM demonstrated greatly reduced photobleaching of single molecules, demonstrating that single molecules can be detected in cells and prove that SPAM preserves spatial resolution of TIRF.

Recently it has become possible to detect signals originating from a single molecule (SMD). Such signals are not averaged over all molecules in a cell and can provide information about kinetic rates, orientation, or motion of proteins. However, to be able to image individual molecules, these measurements have to be carried out on diluted solutions of proteins, typically at nanomolar concentration. In an intact cell, though, proteins are present in μmolar concentrations. Proteins are meant to operate in such crowded environments. Molecular crowding influences protein solubility and conformation in solution and may impose constraints affecting both structure and function of enzymes. It is therefore essential to measure kinetics of single molecules at μmolar concentrations in vivo. The advantages of measuring enzymatic chemistry or mechanics of single molecules in vivo are particularly apparent in the case of muscle. Because of the regular arrangement of actin- and myosin-containing filaments, every molecule of the active enzyme, myosin, has different kinetics depending on its position relative to actin binding site {Eisenberg, 1980 #569}.

To measure fluorescence of a single molecule, one must be able to limit measurements to a very thin section, such that the fluorescent signal comes mainly from the molecule of interest and not from the background. For most molecules, present in a cell at micromolar concentrations, this very thin section must be in the nanometer range, well beyond capability of wide-field microscopes. The introduction of small observational volumes by using diffraction-limited laser beams and confocal detection has made it possible to limit the observational volume to and eliminate much background noise. In the confocal technique, the laser beam is focused to a diffraction limit and scanned across the sample. However, this limits a volume to about a femtoliter ($10^{-15}$ L), still 2 orders of magnitude short of what is needed.

To overcome this, number of super-resolution instruments have been constructed that exceed diffraction limit, such as near field, stimulated emission depletion, structured illumination, and reversible saturable optical fluorescence transitions microscopy. Further, the diffraction limit has been broken by zero-mode waveguides, which consist of small apertures in a metal film deposited on a coverslip. Such apertures act as sources of polariton evanescent waves, so the volume defined by each aperture is limited in the Z-direction by the depth of the evanescent wave (~50-100 nm) and in X- & Y-directions by the size of the aperture. The technique was recently applied to observing single molecule dynamics in living cell membranes. Another way to decrease volume is to use Near-Field Scanning Optical Microscopy (NSOM), in which evanescent wave is produced by passing light through a narrow (50-100 nm) aperture. Single molecules on a surface can be observed in this fashion. However, NSOM is best suited to the observation of cell membranes and not the interior of cells because the near field stretched only a few nanometers beyond the tip of the probe. Moreover, the manufacture of the film with small apertures is complex and expensive and super-resolution instruments are either not commercially available or extremely expensive (e.g. stimulated emission microscope costs millions of dollars).

By incorporating principles of surface plasmon imaging, the observational volume of the SPAM microscope is made extremely small ($10^{-18}$-$10^{-19}$ L), e.g., by placing a sample on a thin metal film and illuminating it with the laser beam directly [reverse Kretschmann (RK) configuration] or through the metal layer [Kretschmann (KR) configuration]. Excitation light produces Propagating Surface Plasmons at the metal layer. The thickness of the detection volume is defined by a distance-dependent coupling with surface plasmons. This distance is typically less than 50 nm, thinner than the scanning confocal microscopes. It is further reduced at a close proximity (below 10 nm) to a surface by quenching by a metal. In KR mode it is even thinner, being a product of evanescent wave penetration depth and distance-dependent coupling with surface plasmons. The extremely thin optical sectioning possible with SPAM and excellent background rejection make it suitable for observation of single molecules.

SPAM is illustrated in FIG. 1 (left). A Surface Plasmon Assisted Microscope 10 is shown. A light beam 12 is incident perpendicularly above a sample 14. Sample 14 may be, e.g., a cell (as depicted) that is placed on a light translucent material 16 (e.g., a coverslip) coated with a metal layer 18 (e.g., thin layer of noble metal). Incident light produces Surface Plasmons propagating along the surface of the metal. These plasmons couple with the light to excite fluorophore 20. Fluorescent light 20 once again couples with the plasmons to emerge at the bottom of the coverslip at the SPCE angle 22 (which is smaller than SPR angle) as a fluorescent emission 24 (often in the form of a ring). The fluorescent emission 24 traversed immersion oil 26 and objective 28 and is detected by a light detector (not depicted). The far field fluorescence 30 is reflected by the metal layer 18 as is the scattered excitation light 32, thereby eliminating the majority of the background. FIG. 1 (right) shows a conventional microscope.

Cover slip 16 can be made from any of a number of materials in the form or a slip, slide or plate and may have any shape (flat, convex, concave) and be made from any at least partially translucent material. Non-limiting examples of at least partially translucent material include silicon, glass, quartz, sapphire, borosilicate glass (e.g., barium or aluminoborosilicate glass), polymers or combinations thereof. Generally, the at least partially translucent material will be a high refractive index material. The metal layer 18 may be deposited, layered, sputtered, electroless plated, chemical vapor deposited, photoreduced, or grown on the at least partially translucent material by any of a number of well-known methods. Non-limiting examples of metals and their alloys include aluminum, silver, gold or copper and combinations thereof. In certain embodiments, e.g., single target, high throughput analysis, the at least partially translucent material may be a string, line or tube on which the metal layer 18 has been at least partially deposited. When a sample is run on the surface of the metal layer 18, individual targets (e.g., cells) traverse the surface at the detection point and are detected one at a time as they reach the microscope objective 28 and are measured one at a time in continuous fashion (similar to a fluorescence activated cell sorter), allowing for detection and even sorting.

Non-limiting examples of targets also include single molecules in a microfluidic environment (e.g., in a tube or as droplets), beads, nanotubes, nanoballs, nanospheres, nanocones, fibers and combinations thereof. Targets for detection may have any shape or form and may include small molecules (organic or inorganic), amino acids, peptides, proteins, polypeptides, nucleic acids, polynucleotides, saccharides (mono, di, tri, tetra, oligo or polymeric), lipids, vitamins, minerals, portions of cells, cells, portions of tissues, tissues and even entire organisms. The targets may include at least portions of viruses, obligate symbiotes, cyanobacteria, bacteria, fungi, plants, animal cells and combinations thereof.

Non-limiting examples of surface plasmon enhanced molecules, such as fluorescent dyes, also include chemiluminescent, bioluminescent, electrochemiluminescent, fluorescent resonance and combinations thereof. Non-limiting examples of light sources for use with the present invention will most often be matched to the type of fluorescence, include white light sources (with or without filters), ultraviolet lamps, lasers (e.g., gas or semiconductor), light emitting diode(s) (LEDs) and combinations thereof.

Non-limiting examples of fluorophores that may be used with the present invention include: 7-Amino-actinomycin D; Acridine orange; Acridine yellow; Alexa Fluor; AnaSpec; Auramine O; Auramine-rhodamine stain; Benzanthrone; 9,10-Bis(phenylethynyl)anthracene; 5,12-Bis(phenylethynyl)naphtacene; CFDA-SE; CFSE; Calcein; Carboxyfluorescein; 1-Chloro-9,10-bis(phenylethynyl)anthracene; 2-Chloro-9,10-bis(phenylethynyl)anthracene; Coumarin; Cyanine; DAPI; Dark quencher; Dioc6; DyLight Fluor; Ethidium bromide; Fluorescein; Fura-2; Fura-2-acetoxymethyl ester; Green fluorescent protein; Hilyte Fluor; Hoechst stain; Indian yellow; Luciferin; Perylene; Phycobilin; Phycoerythrin; Phycoerythrobilin; Propidium iodide; Pyranine; Rhodamine; RiboGreen; Rubrene; Ruthenium(II) tris(bathophenanthroline disulfonate); SYBR Green; Stilbene; TSQ; Texas Red; Umbelliferone; Yellow fluorescent protein, and combinations thereof.

This method has two characteristic features that make it suitable for SMD. First, SPAM has excellent background rejection, made possible by the fact that scattered excitation light is unable to penetrate the metal layer and enter the objective. This is illustrated in FIG. 1 by comparing left and right pictures. In SPAM, the scattered excitation light, which is a predominant problem in single molecule detection, is unable to penetrate the coverslip, because it acts as a simple mirror. In conventional detection, however, scattered light has no difficulty penetrating the coverslip and entering the objective. The light beam 12, will generally be a controlled or coherent light source, e.g., a laser or other light source that matches with excitation and emissions of any of a number of fluorescence dyes.

In operation, the SPAM microscope of FIG. 1, shows the sample 12 (in this rendering a cell) that is illuminated from above. The cell is placed or grown on the metal layer 18 coated light translucent material 16 and excited with green light (light beam 12). The excitation energy couples to the surface plasmons and radiates to the objective (red) as a surface of a cone with half angle equal to the SPCE angle. Metal layer 18 can be, e.g., a thin layer of Al (up to 20, 30, 40, 50 or 100 nm thick) or Ag or Au (up to 20, 30, 40, 50, 100, 150 nm thick). The scattered light 32 is unable to penetrate the light translucent material 16 and is radiated into free space. In conventional microscope (FIG. 1 right), there is no directional radiation and scattered light is able to penetrate the coverslip.

Second, the coupling of the fluorescence is strongly distance dependent and extends only to about fifty nanometers into a sample. The effective distance is reduced well below 100-200 nm characteristic of TIRF (in the case of Kretchmann excitation it is product of evanescent excitation and distance-dependent emission coupling). It is further reduced at close proximity (below 10 nm) to a surface by quenching by a metal. It is important to note that coupling very well preserves spectral properties of fluorophores.

Another feature of SPAM is that fluorescence coupling to surface plasmons dramatically depends on the orientation of the molecule transition moment, i.e., the method is particularly suited to measurements of protein orientation changes.

SPAM can be built in two general configurations: in Reverse Kretchmann (RK) configuration as described above, when the laser beam strikes a cell directly, and in Kretchmann configuration (KR) where the laser beam strikes a sample from below at SPR angle. RK has the advantages that it avoids losses of intensity due to penetration of mirrored surface (metal layer 18 on light translucent material 16), it does not require expensive TIRF high NA objective to collect fluorescence, it avoids losses inherent in a dichroic mirror, and it is simpler and less expensive to implement. KR has the advantage that SPR illumination excites evanescent wave at the glass-buffer interface. This makes the optical sectioning thinner because it is now a product of two near-field factors: the depth of evanescent wave excitation and a distance-dependent coupling of excited fluorophores to the surface plasmons.

Comparison to TIRF. Until now, the method of choice to image single molecules in cells has been TIRF microscopy, because of its good background rejection. TIR excitation is widely used in cell biology. TIR excitation of fluorescence at a glass/buffer interface is used for selectively detecting fluorophores at the interface. Many variations of the technique have been described for applications in cell biology single molecule detection and surface biophysics. Prismless TIR illumination is known to have significant background fluorescence excited by subcritical angle light scattering. Alternative TIR illumination schemes using a prism to introduce excitation light to the glass/water interface at greater than the critical angle, lower the background levels but add the complication of a prism.

It has been found that the background rejection and thickness of optical section of SPAM are at least 10 and 3 times better than TIRF. Moreover, the cost of SPAM (~$15K) is significantly less than the cost of an inverted fluorescence microscope including a TIRF attachment ($44,078, 51,564, 41,768 by Olympus, Zeiss and Nikon, respectively). SPAM also provides superior background suppression in the bulk. SPAM collects signals from exceedingly thin section of sample, has reduced photobleaching of single molecules, is able to detect single molecules in cells and has equivalent spatial resolution to that of TIRF.

Background rejection in bulk. SPAM showed superior suppression of background fluorescence in the bulk. As mentioned before, it results from that does not couple to plasmons arises from the directional nature of the emitted light and the presence of the opaque metal film. Background suppression in 4 different configurations shown in FIG. 2 was measured. In the RK configuration, the sample is excited directly. The excited fluorophores either emit fluorescence or couple to the surface plasmons (at a very close distance, less than 10 nm, the fluorescence is being quenched by the metal). The energy coupled to the surface plasmons can be radiated into glass at an SPCE angle. In the KR configuration, the excitation comes through the glass prism. At the angle close to SPR, the p-polarized light is being absorbed by surface plasmons. The strong evanescent field from propagating plasmons excites fluorophores near the silver surface. It is intuitively obvious that the far-field fluorescence will be partially blocked by the opaque mirror and will minimally interfere with observed SPCE. SPCE originates from near-field interaction of excited fluorophores with surface plasmons localized in metal/dielectric interface.

Figure 2:
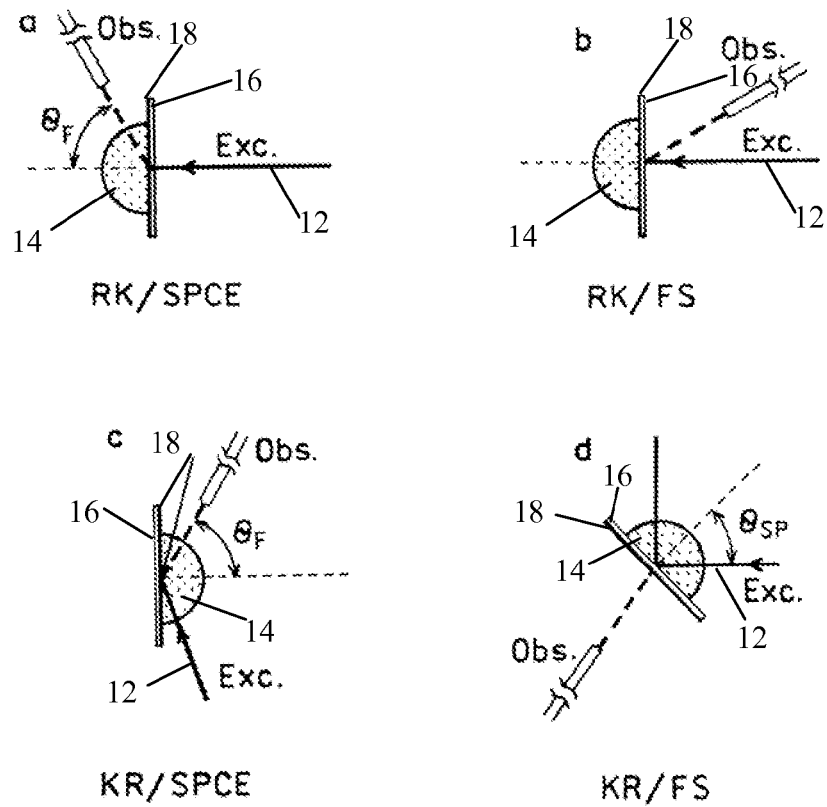
FIG. 2 shows various geometrical arrangements used to measure background suppression of the present invention.

FIG. 2. Geometrical arrangements used to measure background suppression. FIG. 2a—RK excitation, SPCE observation; FIG. 2b—RK excitation, Free Space (FS) observation; FIG. 2c—KR excitation, SPCE observation; d—KR excitation, FS observation.

Figure 3:
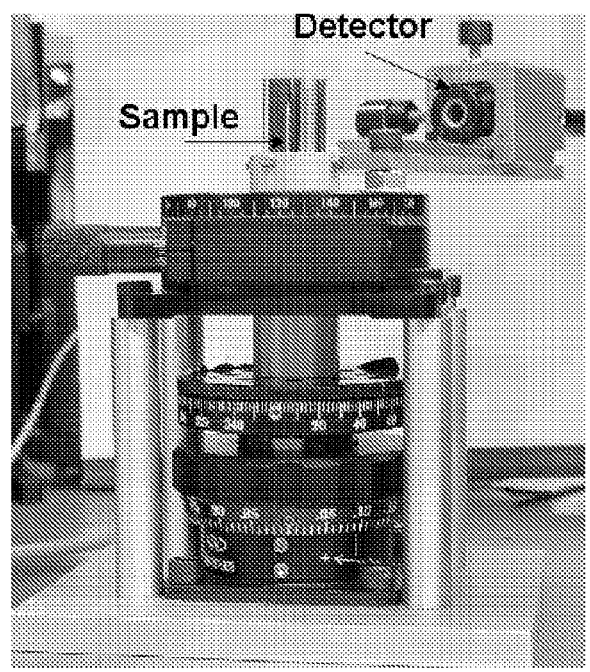
FIG. 3 shows a Surface Plasmon Coupled Emission (SPCE) goniometer.
Figure 4:
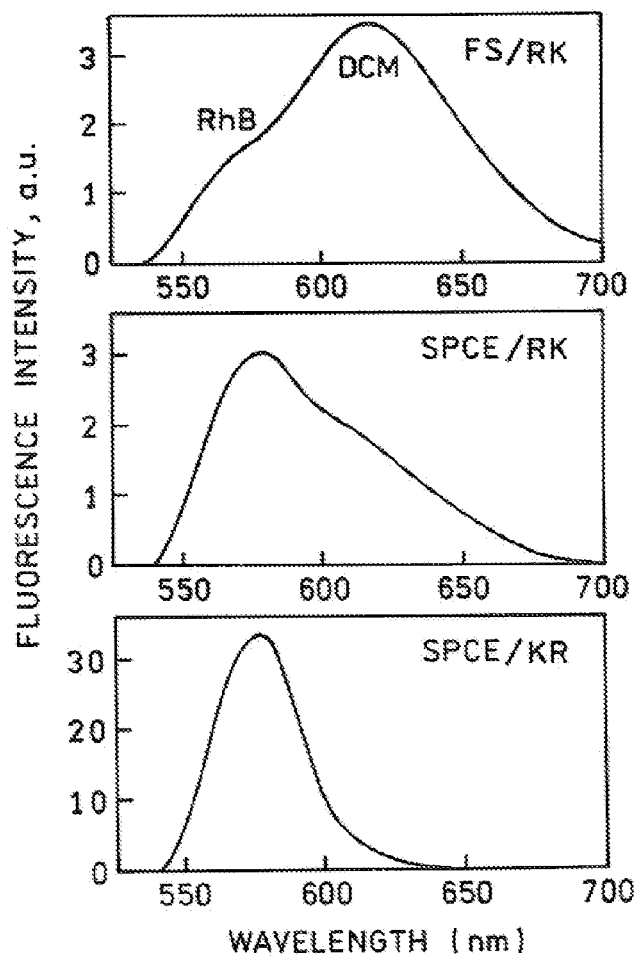
FIG. 4 shows fluorescence spectra of the rhodamine B (RhB) in the presence of a background (4-(Dicyanomethylene)-2-methyl-6-(p-dimethylaminostyryl)4H-pyran (DCM) in Ethanol) measured at various observation/excitation configurations. Top: Emission spectrum observed at a small angle from the excitation in RK configuration. This free space (FS) spectrum is dominated by a background DCM emission. The RhB emission at 575 nm is minimal. Middle: In the same (as in a top panel) RK configuration the observation was made from the prism side at the SPCE angle. In this case the dominant emission is from the RhB and DCM background is greatly suppressed. Bottom: The sample was rotated to the KR configuration and the excitation was at a SPR angle.

To observe fluorescence, goniometer was constructed a shown in FIG. 3. To see the depth of the distance-dependent coupling, we combined the sample with a background. The sample, a 22 nm layer of poly(vinyl)alcohol(PVA) doped with rhodamine B (RhB), was deposited on a silvered side of the glass slide—a part of a demountable cuvette (0.1 mm, Sarna). The role of background plays the 100 micron layer of ethanol solution of DCM (4-(Dicyanomethylene)-2-methyl-6-(p-dimethylaminostyryl)4H-pyran, Kodak), which was added to the demountable cuvette. The fluorescence of DCM is shifted by ~50 nm to the longer wavelengths and is easily distinguishable from the RhB emission. With RK configuration, the Free Space (FS) signal is dominated by the DCM fluorescence (FIG. 4, top). This was adjusted by the DCM concentration.

FIG. 3 shows a SPCE goniometer. Sample fluorescence at different angles is detected by a photodetector. Sample is illuminated from the front by the green laser.

In this configuration both, the background and the sample are being excited homogenously, and no surface plasmons are induced by the excitation light. In the direction of SPCE, the observed spectrum is dominated by RhB fluorescence (FIG. 4, middle). Only a small fraction of excited DCM fluorophores are able to couple to the surface plasmons, namely these which were within the proper distance from the silver surface. Next, we rotated the prism and sample to the KR configuration. In this case, the observed SPCE is almost not perturbed by the DCM background. This happen because two factors have been combined, the distance-dependent coupling and distance-dependent excitation by the evanescent field. In the rough approximation, the effect of detection volume minimization is a product of described above two factors. This is a unique future of SPCE, not achievable in the total internal reflection fluorescence (TIRF), where both near- and far-field couple to the surface.

FIG. 4 shows the fluorescence spectra of the RhB in the presence of a background (DCM in Ethanol) measured at various observation/excitation configurations. FIG. 4 Top: Emission spectrum observed at a small angle from the excitation in RK configuration. This free space (FS) spectrum is dominated by a background DCM emission. The RhB emission at 575 nm is minimal. Middle: In the same (as in a top panel) RK configuration the observation was made from the prism side at the SPCE angle. In this case the dominant emission is from the RhB and DCM background is greatly suppressed. FIG. 4 Bottom: The sample was rotated to the KR configuration an the excitation was at a SPR angle. The observation was adjusted to the SPCE angle. Now, essentially only RhB emission is present in the spectrum. Note also that the intensity of the SPCE signal in KR configuration is an order of magnitude greater than the intensity in RK configuration.

Background rejection by SPAM. The superior rejection of background was demonstrated by comparing performance of SPAM with TIRF and Transmission microscope. The SPAM microscope had an excitation at 633 nm from 35 mW HeNe laser (Coherent 31-2140-000). The fluorescent light was collected by the objective (60×, NA=1.45, PlanApo, Olymus) at the SPCE angle, stripped of the incident light wavelengths by the barrier filter and focused by a tube lens on a surface of EM CCD camera (Hamamatsu EMImage).

Figure 5:
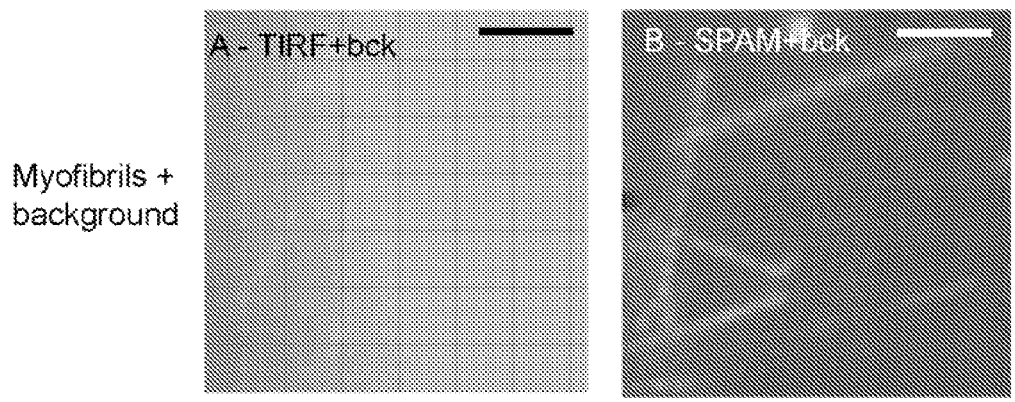
FIG. 5 shows the background rejection by SPAM in KR configuration. 0.5 mM Rhodamine 800 added as background obscures the image in ordinary Total Internal Reflection Fluorescence (TIRF) (FIG. 5A). SPAM eliminates the contribution from background (FIG. 5B). Myofibrils (0.1 mg/mL) were labeled with 100 nM rhodamine-phalloidin+10 μM unlabeled phalloidin for 5 min at room temperature, then extensively washed with rigor buffer containing 50 mM KCl, 2 mM $MgCl_2$, 1 mM DTT, 10 mM TRIS pH 7.0. 532 nm excitation. 1.65 NA×100 Olympus objective, sapphire substrate, 1.78 Refractive Index immersion oil. The bars are 5 μm.
Figure 16:
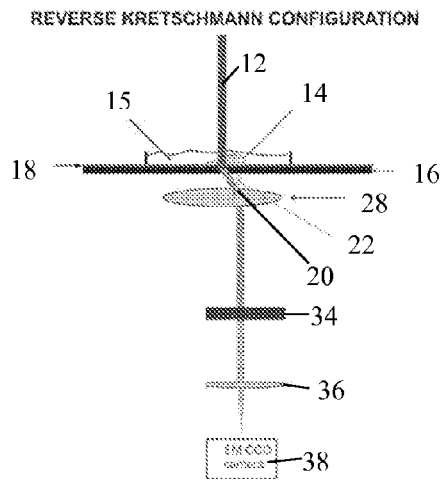
FIG. 16 is a schematic (left) and prototype (right) of the microscope. The excitation light path for RK configurations is shown in red.

Comparison of SPAM (KR configuration) with TIRF microscope. FIG. 5 compares TIRF and SPAM images of skeletal muscle myofibrils. Prototype SPAM was used in KR configuration (FIG. 16). High NA objective (Olympus Apo NA=1.65) was used in these experiments. It required the use of high refractive index sapphire substrate. Control studies show that myofibrils look normal under Nomarski and TIRF (not shown) illumination. However, when the background was added (0.5 mM of Rhodamine 800), the fluorescence was completely dominated by the background (A). When image was observed by SPAM under KR configuration, however, the image was no longer dominated by the background (B). The scans at the bottom through the myfibril at left show that S/N ratio is at least 6 times better for SPAM than TIRF.

FIG. 5 demonstrates the background rejection by SPAM in KR configuration. 0.5 mM Rhodamine 800 added as background obscures the image in ordinary TIRF (FIG. 5A). SPAM eliminates the contribution from background (FIG. 5B). Myofibrils (0.1 mg/mL) were labeled with 100 nM rhodamine-phalloidin+10 μM unlabeled phalloidin for 5 min at room temperature, then extensively washed with rigor buffer containing 50 mM KCl, 2 mM $MgCl_2$, 1 mM DTT, 10 mM TRIS pH 7.0. 532 nm excitation. 1.65 NA×100 Olympus objective, sapphire substrate, 1.78 Refractive Index immersion oil. The bars are 5 μm.

Figure 6:
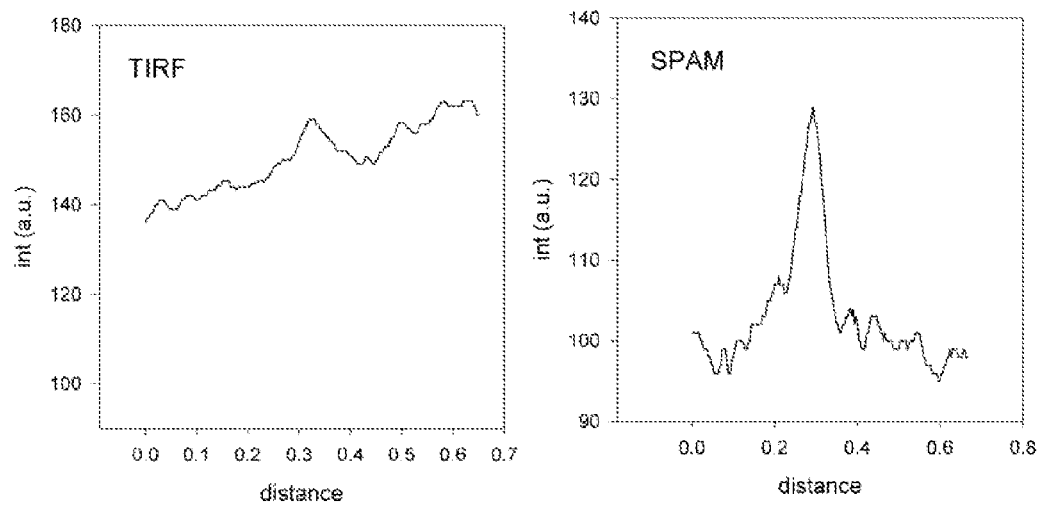
FIG. 6 shows profiles of a myofibril in TIRF (left) and SPAM (right) images to show the difference in S/N ratio. For chosen myofibrils it was 10.

The difference is quantified in FIG. 6, which compares the profile across a visible myofibril in TIRF image (left) with the profile across myofibril in SPAM image (right). The S/N ratio, defined as the ratio of peak intensity to the background was 4% and 40% for TIRF and SPAM images, respectively.

FIG. 6. Profiles of a myofibril in TIRF (left) and SPAM (right) images to show the difference in S/N ratio. For chosen myofibrils it was 10.

Figure 7:
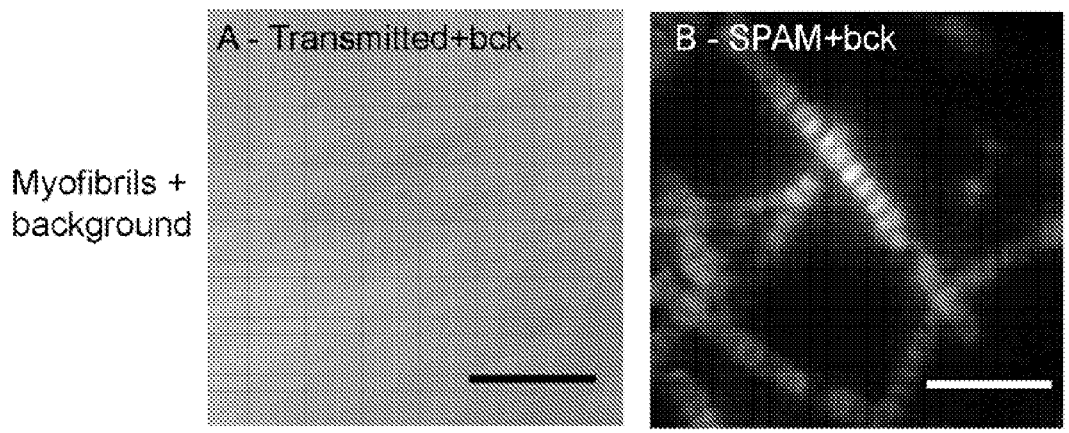
FIG. 7 shows the background rejection by SPAM in RK configuration. Addition of 0.5 mM Rhodamine 800 background completely obscures the image in ordinary Transmitted light (FIG. 7A), the SPAM image using RK configuration is no longer completely dominated by identical concentration of the background (FIG. 7B). Myofibrils (0.1 mg/mL) were labeled with 100 nM Alexa647-phalloidin+10 μM unlabeled phalloidin for 5 min at room temperature, then extensively washed with rigor buffer. 633 nm excitation. 1.45 NA×100 Olympus objective (PlanApo), glass substrate, 1.518 Refractive Index immersion oil. Bars are 10 μm.

Comparison of SPAM (RK configuration) with transmission microscope. FIG. 7 compares Transmission and SPAM images of skeletal muscle myofibrils. Prototype SPAM was used in RK configuration (see FIG. 16). Control experiments show that myofibrils look normal under Nomarski and Transmitted light configuration (not shown) illumination. However, when the background in the form of 0.5 mM Rhodamine 800 was added, the fluorescence was completely dominated by the background (A). When image was observed by SPAM under RK configuration, however, the image was no longer dominated by the background (B).

FIG. 7 shows the background rejection by SPAM in RK configuration. Addition of 0.5 mM Rhodamine 800 background completely obscures the image in ordinary Transmitted light (FIG. 7A), the SPAM image using RK configuration is no longer completely dominated by identical concentration of the background (FIG. 7B). Myofibrils (0.1 mg/mL) were labeled with 100 nM Alexa647-phalloidin+10 μM unlabeled phalloidin for 5 min at room temperature, then extensively washed with rigor buffer. 633 nm excitation. 1.45 NA×100 Olympus objective (PlanApo), glass substrate, 1.518 Refractive Index immersion oil. Bars are 10 μm.

Figure 8:
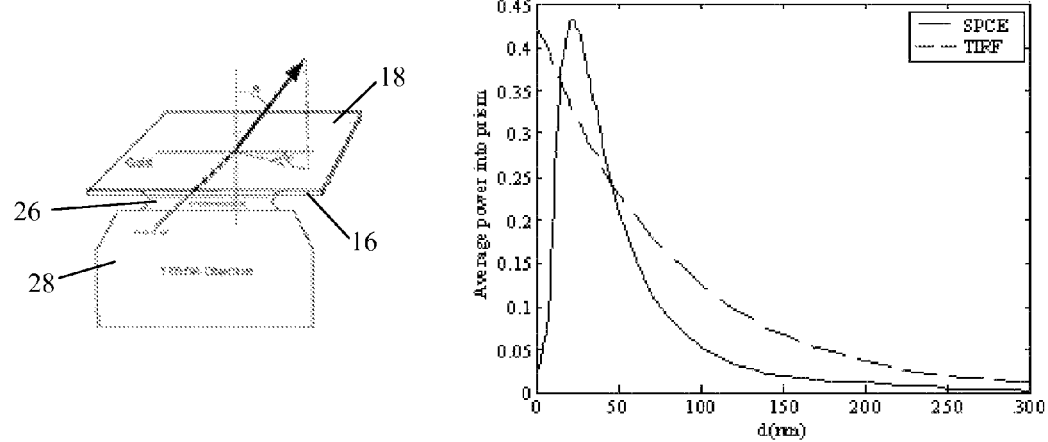
FIG. 8. Left: Definition of angles. Right: Calculated power flow to the objective in the SPCE experiments for s-orientation of the transition moment. The time between excitation of the fluorophores is assumed much longer than the emission time. Gold layer of 48 nm, excitation wavelength=633 nm, at maximum field (57.86°), emission at 670 nm. Solid line-SPCE. Broken line-TIRF. The strong dissipation of energy into the metal layer for short distances lowers the power in the SPCE, but not TIRF case.

SPAM provides extremely thin optical sectioning. Excellent background rejection is the first necessary condition to image single molecules. The second is the good optical sectioning. We calculate here the distance from which SPAM collects the signal. This distance depends on the orientation of the transition moment of a fluorophores. Let us define the polar angle of the fluorophore transition moment ($\Theta$) and the azimuthal angle ($\phi$) as usual (FIG. 8, left). On the right is the average power of SPCE emission versus the distance of the fluorophore from the metal. The metallic layer considered here is 48 nm thick layer of gold deposited on high refractive index glass (n=1.78). The refractive index of medium was taken as 1.37 to mimic that of muscle. The excitation was at 633 in Kretschmann configuration, emission=670 nm. The distance dependence is no longer exponential. The half widths of the SPCE fluorescence volume is 40 nm for parallel dipoles. Since fluorescence is totally quenched from the volume within 10 nm from the interface, we estimate that fluorescence as originating from layer 50 nm-20 nm thick.

FIG. 8. Left: Definition of angles. Right: Calculated power flow to the objective in the SPCE experiments for s-orientation of the transition moment. The time between excitation of the fluorophores is assumed much longer than the emission time. Gold layer of 48 nm, excitation wavelength=633 nm, at maximum field (57.86°), emission at 670 nm. Solid line-SPCE. Broken line-TIRF. The strong dissipation of energy into the metal layer for short distances lowers the power in the SPCE, but not TIRF case.

Figure 9:
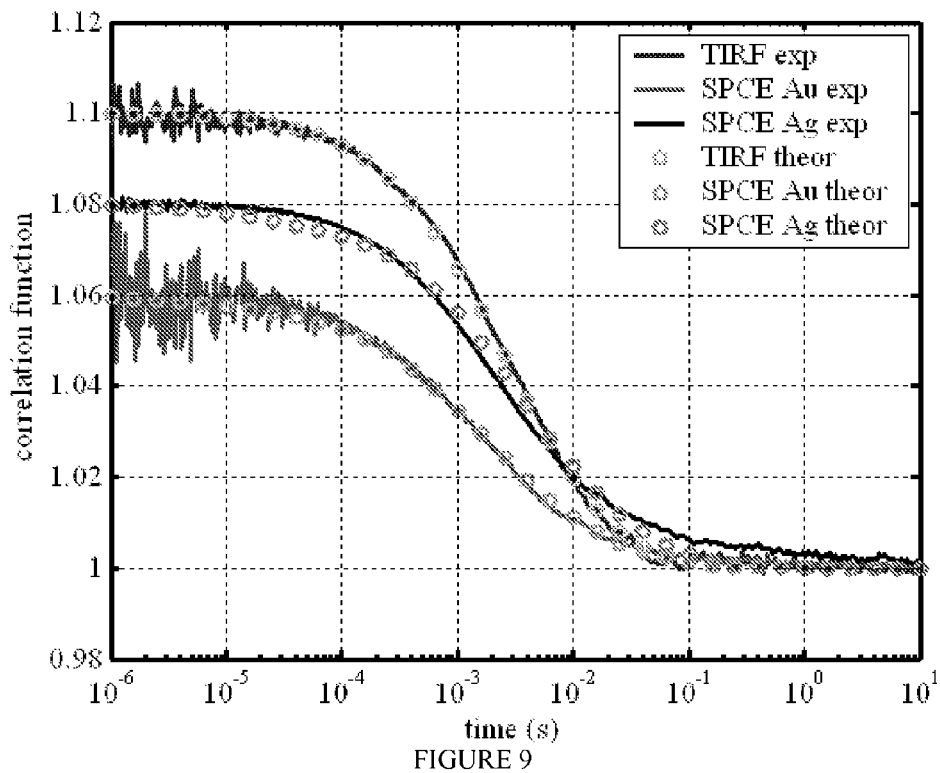
FIG. 9 shows the fit of theoretical FCS curves to experimental data. Single-exponential for TIRF and bi-exponential for SPCE. Note that the y-axis is linear.

To check the results of calculations, the distance was measured. This was estimated for 50 nm gold coverslips using Fluorescence Correlation Spectroscopy (FCS). In this technique, one forms a small detection volume and follows number fluctuations of fluorescence intensity of a fluorophore as it diffuses in- and out-of the detection volume. The size of the volume can be estimated from the rate of decay of autocorrelation function of fluctuations. Faster decay of autocorrelation function indicates faster fluctuations, i.e., smaller volume from which fluorescent molecules can diffuse in and out. Many researchers followed FCS in a microscope. Recently, the FCS method was used in the TIRF microscope. Suspension of 0.1 μm diameter microspheres (Molecular Probes, Eugene, Oreg.) was diluted 100× to $3.6 \times 10^8$ spheres/mL. The spheres were placed on a coverslip coated with gold. The intensities were measured in 160 μs intervals for 30 sec. The theoretical expression for correlation function is where $\omega_{xy}=2\sigma$ is the lateral radius of the confocal aperture on the image:

$$G(t) = 1 + \frac{1}{2N} \frac{d_0 R_{00}(t) - 4\frac{d_0 d_1}{d_0 + d_1} R_{01}(t) + d_1 R_{11}(t)}{d_0 - 4\frac{d_0 d_1}{d_0 + d_1} + d_1}$$

$$R_{nn}(t) = \left(1 + \frac{Dt}{\sigma^2}\right)^{-1}\left[\left(1 - \frac{2Dt}{d_n^2}\right)\mathrm{erfc}\left(\sqrt{\frac{Dt}{d_n^2}}\right)\exp\left(\frac{Dt}{d_n^2}\right) + \sqrt{\frac{4Dt}{\pi d_n^2}}\right]$$

$$R_{nm}(t) = \left(1 + \frac{Dt}{\sigma^2}\right)^{-1}\left(\frac{d_m}{d_m - d_n}\mathrm{erfc}\left(\sqrt{\frac{Dt}{d_m^2}}\right)\exp\left(\frac{Dt}{d_m^2}\right) + \frac{d_n}{d_n - d_m}\mathrm{erfc}\left(\sqrt{\frac{Dt}{d_n^2}}\right)\exp\left(\frac{Dt}{d_n^2}\right)\right)$$

plane, and d is the rms thickness of the detection volume. The fit of the above equation to the correlation function is shown in FIG. 9. For SPCE with gold the best fit gave $d_0=35$ nm, $d_1=10$ nm, $d=\sqrt{d_0^2+d_1^2}=36.4$ nm (RMS value).

FIG. 9 fits theoretical FCS curves to study data. Single-exponential for TIRF and bi-exponential for SPCE. Note that the y-axis is linear.

Spam reduces photobleaching of single molecules. The effect is best illustrated by comparing the time course of photobleaching of single molecules of rhodamine dye on glass viewed by TIRF, with the time course of photobleaching of the same molecules on gold viewed by SPAM. Every molecule in FIG. 10 (TIRF) bleached within 10-40 sec from the moment the light impinged on it, whereas in FIG. 11 (SPAM in KR configuration) the molecule bleached ~25% in 100 sec.

Figure 10:
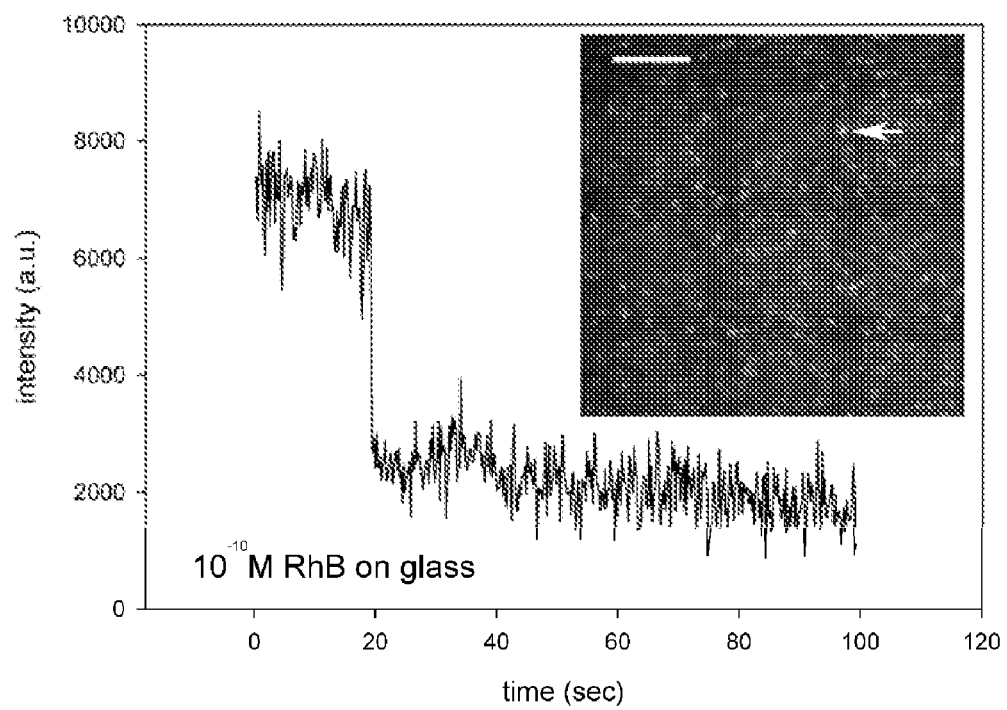
FIG. 10 shows a time course of fluorescence of a single molecule of RhB on glass. The molecule analyzed (pointed to by the arrow in the inset) is shown at time 0. $10^{-10}$M RhB was spin-coated on a glass coverslip in the presence of 2% Poly-Vinyl-Alcohol (PVA). 1.45 NA, 60× objective, RI=1.518 immersion oil. The background has been subtracted. Bar is 10 μm.

FIG. 10 is a time course of fluorescence of a single molecule of RhB on glass. The molecule analyzed (pointed to by the arrow in the inset) is shown at time 0. $10^{-10}$M RhB was spin-coated on a glass coverslip in the presence of 2% Poly-Vinyl-Alcohol (PVA). 1.45 NA, 60× objective, RI=1.518 immersion oil. The background has been subtracted. Bar is 10 μm.

Figure 11:
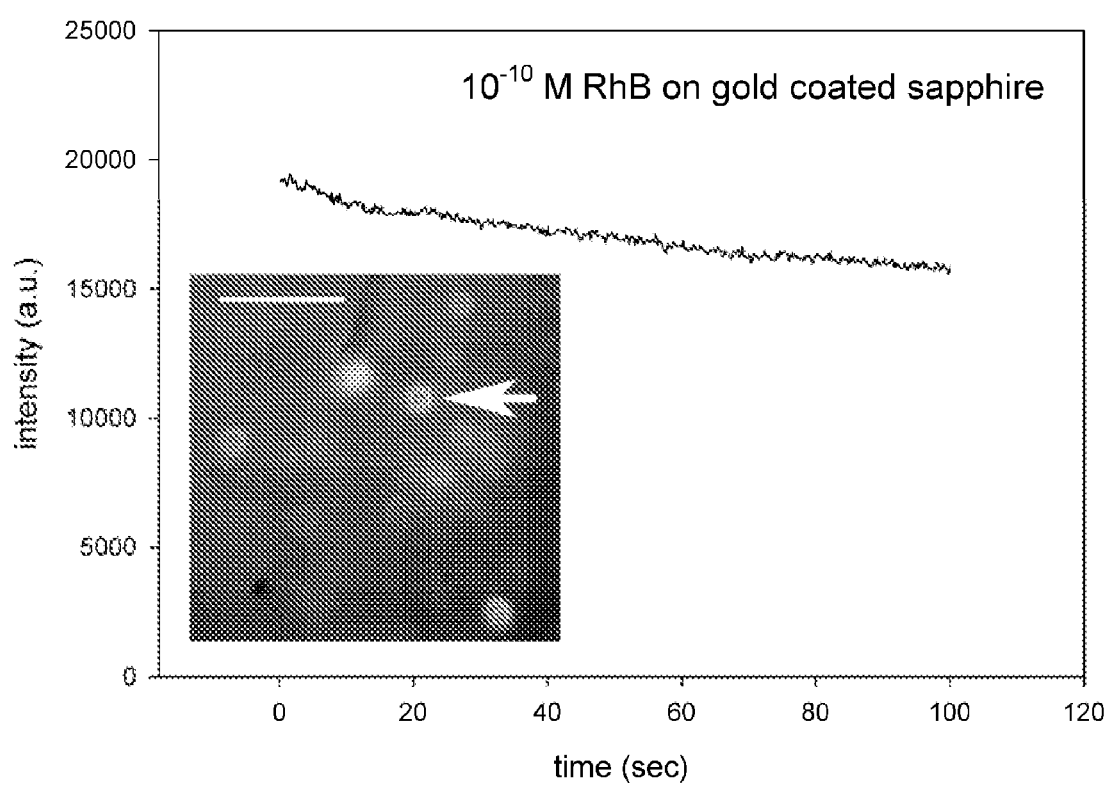
FIG. 11 shows the time course of fluorescence of a single molecule of RhB on gold coated coverslip. The molecule analyzed (pointed to by the arrow in the inset) is shown at time 0. $10^{-10}$M RhB was spin-coated on a sapphire coverslip in the presence of 2% PVA. 1.65 NA, 100× objective, 1.78 immersion oil. The background has been subtracted. Bar is 10 μm.

FIG. 11 is a time course of fluorescence of a single molecule of RhB on gold coated coverslip. The molecule analyzed (pointed to by the arrow in the inset) is shown at time 0. $10^{-10}$M RhB was spin-coated on a sapphire coverslip in the presence of 2% PVA. 1.65 NA, 100× objective, 1.78 immersion oil. The background has been subtracted. Bar is 10 μm.

As an example, but by no means a limitation of the present invention, it is hypothesized that the reduced photobleaching is due to depletion of a triplet state. Fluorophores on glass decay from the excited state by fluorescence, by dark transitions and by transitions to triplet state. It makes sense to believe that photobleaching occurs predominantly in the triplet state, because fluorophores spend a long time in this state and so have a good chance to be attacked by oxygen. It may be predicted that phosphorescence lifetime of a fluorophore on metal is significantly decreased in comparison with fluorophore on glass. This hypothesis would explain the slow bleaching seen in FIG. 11; it is being tested at present.

Figure 12:
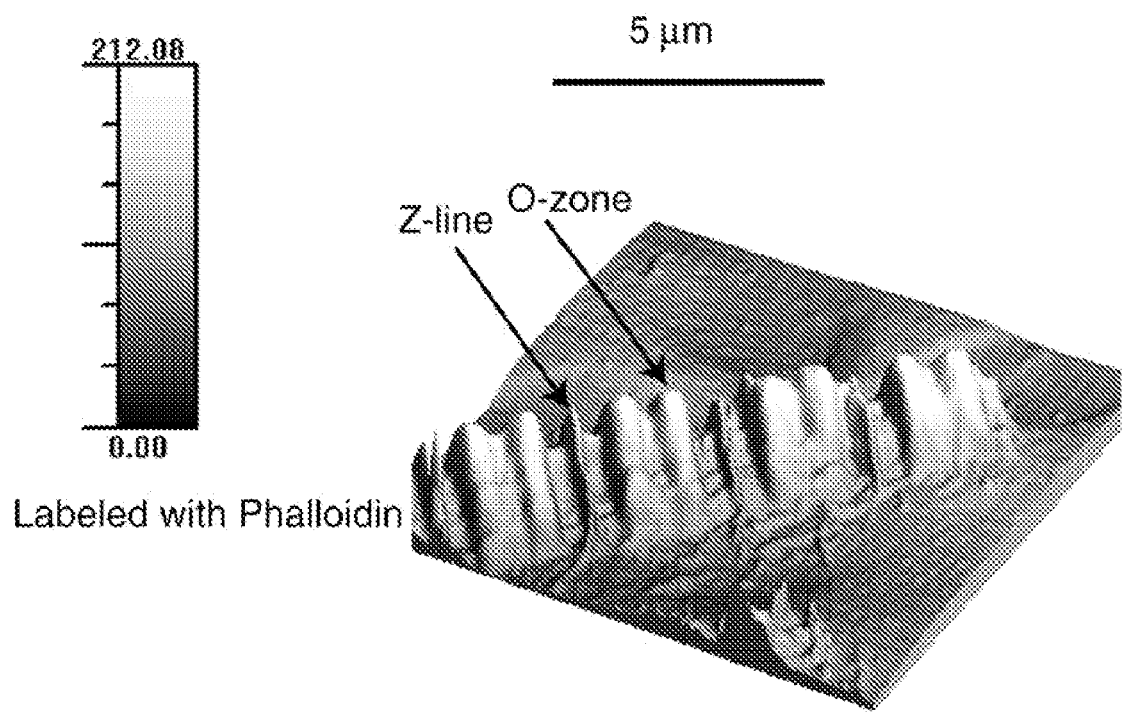
FIG. 12 is an AFM image of a myofibril on gold coated coverslip. The X-Y dimensions are indicated by the bar, the Z dimension (in nm) by the color bar at the left.

Single molecule detection in muscle. Having shown excellent background rejection and optical sectioning properties, we were ready to test SMD ability of SPAM. For the reasons outlined earlier, skeletal muscle myofibrils were used as an example of biological material. To estimate the number of fluorescent molecules detected by SPAM, it is necessary to know the volume of muscle sarcomere. FIG. 12 shows AFM images of phalloidin-rhodamine labeled myofibril. The AFM image reports on the resistance to stress encountered by the atomic probe. Because phalloidin binding makes the ends of thin filaments stiffer, this region of sarcomere is more difficult for atomic probe to deform. It is known that the pattern of phalloidin labeling changes with time. Initially only the ends of thin filaments are labeled. Redistribution of phalloidin to the I-band takes several hours. Myofibrils used here were observed 5-15 min after labeling, so only the ends of thin filaments were labeled.

FIG. 12 is an AFM image of a myofibril on gold coated coverslip. The X-Y dimensions are indicated by the bar, the Z dimension (in nm) by the color bar at the left.

Figure 13:
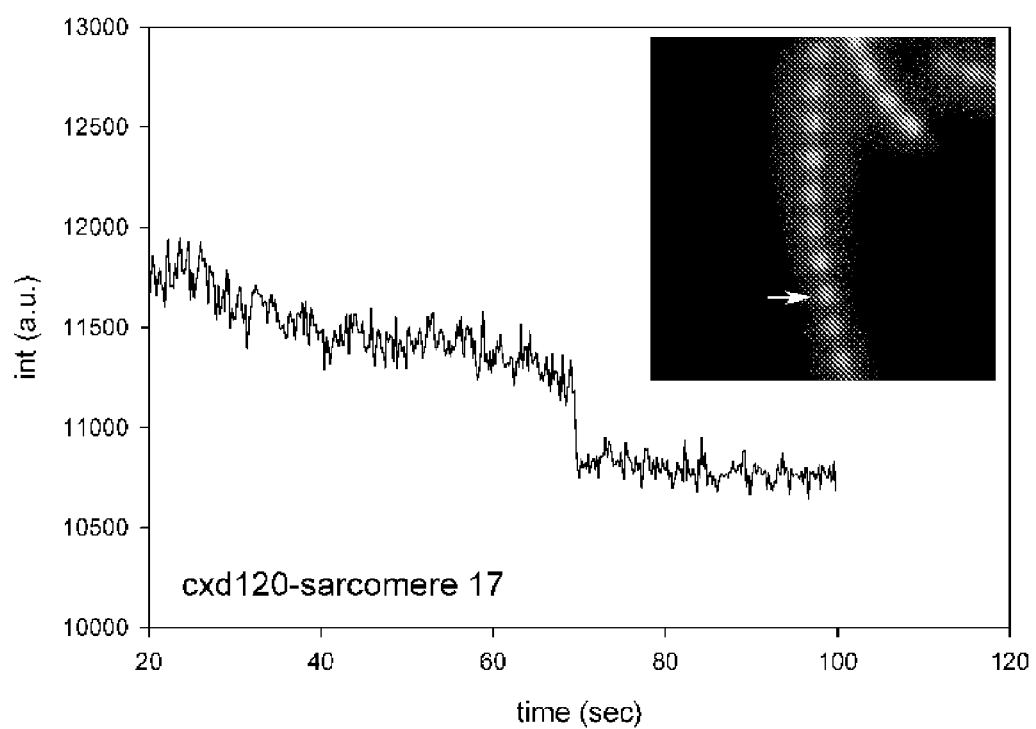
FIG. 13 shows a time course of photobleaching of the O-band pointed to by the arrow in the inset showing the presence of a discrete step corresponding to photobleaching of a single molecule of rhodamine. Other O-bands in this frame also bleached in step-wise fashion.

The average height of 12 phalloidin labeled myofibrils was 97±4 nm (mean+SEM). The typical width and length of a sarcomere are 0.8 and 2.5 μm, respectively, so the typical volume of half-sarcomere is ~0.1 μm$^3$=0.1×10$^{-15}$ L. Since the concentration of actin in muscle is 0.6 mM, this volume contains on average 0.4×10$^5$ actin monomers. The SPAM illumination reaches only the height of 35 nm (~⅓ of a sarcomere, see above). Myofibrils were labeled with 10 nM RP (+9.9 μM non-fluorescent label), i.e. only 10 actin monomers per half-sarcomere were fluorescent. FIG. 13 shows the time course of photobleaching of myofibrils labeled with 10 nM RP+9.9 μM UP. 500 images were captured every 200 ms; the HCImage software (Hamamatsu) was used to calculate the intensity of each sarcomere at each frame. Rectangular Region-of-Interest was created corresponding to each O-band in a 512×512 image. The Intensity Measurement tool was used to measure mean gray value of all the defined ROI's in all 500 images. ROI was 4×4 pixels (slightly smaller than half-sarcomere). This data was saved as tabbed text file. The ASCII file was plotted in SigmaPlot (Systat, San Jose, Calif.). The first frame is shown in the inset. The time course of photobleaching corresponds to change of intensity of the sarcomere pointed to by the arrow in the inset.

FIG. 13 show a time course of photobleaching of the O-band pointed to by the arrow in the inset showing the presence of a discrete step corresponding to photobleaching of a single molecule of rhodamine. Other O-bands in this frame also bleached in step-wise fashion. FIG. 13 shows the sarcomere bleached in step-wise fashion. It suggests the presence of single discrete steps. The number of steps was smaller than calculated number of fluorescent molecules (10). It is possible that the effect observed, but by no means a limitation, that the fluorophores were at different distances from the surface of the coverslip and were thus subjected to different strengths of exciting evanescent wave. The pattern of photobleaching varied from O-band to O-band. Even the O-bands immediately adjoining each other gave different patterns. For example, the O-band immediately to the right of the one pointed to by an arrow in FIG. 13 suggested that bleaching occurred in 4 steps.

Figure 14:
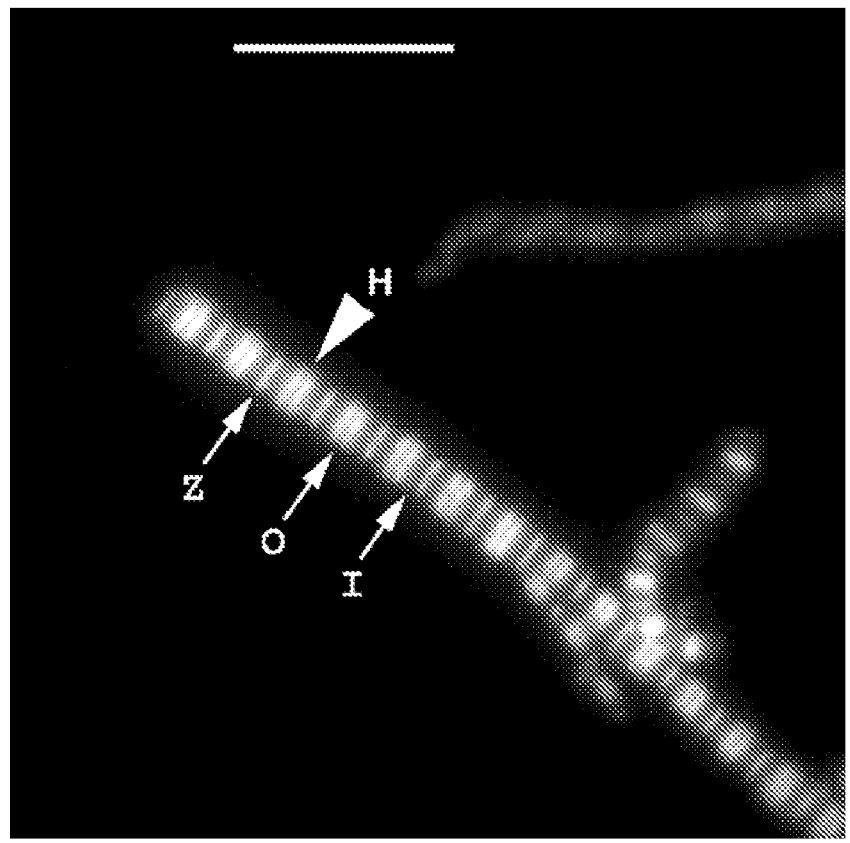
FIG. 14 is a SPAM image of myofibril in rigor. Myofibrillar actin labeled with 0.1 μM fluorescein-phalloidin. Image taken on gold coverslip. The image was contrast enhanced to emphasize superior resolution of the method. Arrows indicate the Z-line, the overlap zone, and the I-band. Arrowhead indicates the H-zone. Bar is 10 μm.

Testing spatial resolution. It is possible that refraction of light by a metal layer distorts the image. Resolution is severely affected when the surface is a discontinuous multi-layer of metal nanoparticles. This is a severe disadvantage of the use of metal surfaces in SMD, because maximal optical resolution is important in resolving single molecules. Optimal resolution allows accurate definition of the Region-of-Interest (ROI) within a cell, a requirement crucial for determination of a function of a specific subcellular organelle. Skeletal myofibril is useful sample to measure optical resolution of biological samples because it contains number of submicron structures of well defined width. FIG. 14 shows that continuous metal surface does not affect the optical resolution. On the left is the SPAM image of a rigor myofibril. Actin was fluorescently labeled with rhodamine-phalloidin. Z-line is a submicron area where barbed ends of actin filaments originate. O-band is submicron area where thin and thick filaments overlap. This area, known as the overlap zone, spans the distance of 0.7-0.3 µm in resting length myofibrils. In studying mechanism of muscle contraction, it is important to place ROI exactly at the area where actin and myosin filaments interact to produce contractile force. In the middle of O-band is the area not containing actin, where myosin filaments are alone.

FIG. 14. SPAM image of myofibril in rigor. Myofibrillar actin labeled with 0.1 µM fluorescein-phalloidin. Image taken on gold coverslip. The image was contrast enhanced to emphasize superior resolution of the method. Arrows indicate the Z-line, the overlap zone, and the I-band. Arrowhead indicates the H-zone. Bar is 10 µm.

Figure 15:
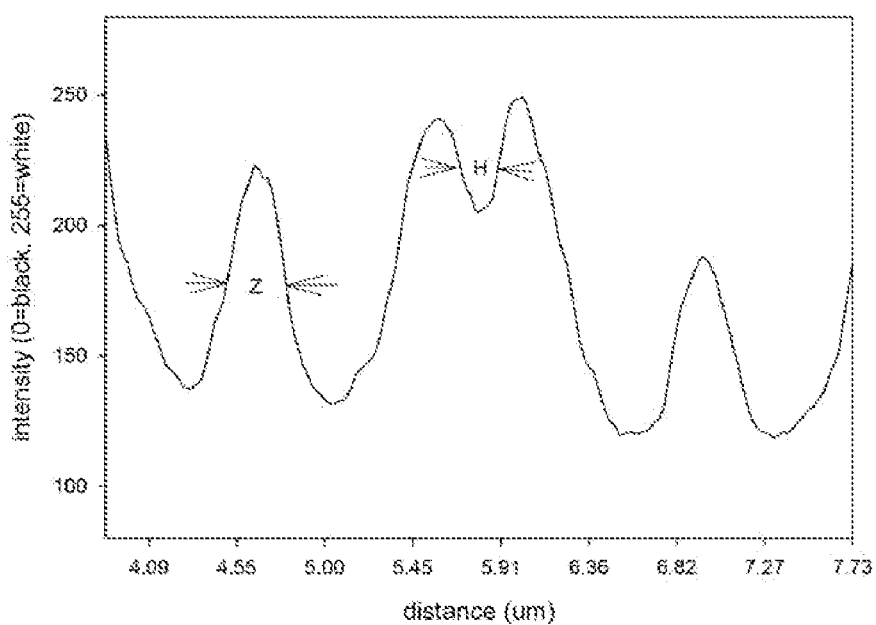
FIG. 15 shows the scan across the sarcomere whose H-zone is indicated in this figure. The image is of good quality, as expected from the near-field method. The widths of the Z-line and H-zone measured by EM are 0.050 and 0.15-0.20 μm, respectively. The full widths at half height (FWHH) measured in SPAM are 0.30 and 0.21 μm, respectively.

FIG. 15 shows the scan across the sarcomere whose H-zone is indicated in this figure. The image is of good quality, as expected from the near-field method. The widths of the Z-line and H-zone measured by EM are 0.050 and 0.15-0.20 µm, respectively {Squire, 1990 #1037}. The full widths at half height (FWHH) measured in SPAM are 0.30 and 0.21 µm, respectively, FIG. 15. Scan across the third sarcomere from the NW end of myofibril indicated by H in FIG. 14, suggesting that full optical resolution has been reached. This is in spite of the fact that the image has been undersampled by a factor of 1.8: the pixel size of the camera is 16 µm×16 µm. For the 100× NA 1.65, 100× objective and 532 nm illumination, the back projected size of the pixel of the camera is 16 µm/100=160 nm. The Rayleigh resolution limit is ~200 nm. According to the Nyquist sampling theorem, the ideal spatial sampling rate should have been 200/2.3≈90 nm. Therefore the images are under-sampled by a factor of 160/90≈1.8. Under-sampling allows the light to be concentrated on fewer pixels. Under the present low-light conditions, this creates a signal that has greater amplitude relative to the background noise, and therefore boosts Signal-to-Noise (S/N) ratio.

Reverse Kretchmann implementation of SPAM. As mentioned before, this configuration (FIG. 16) has the advantages that it avoids losses of intensity due to penetration of mirrored surface (metal layer 18 on light translucent material 16), it does not require expensive TIRF high NA objective to collect fluorescence, it avoids losses inherent in a dichroic mirror, and it is simpler and less expensive to implement. The 633, 532 or 488 laser lines are delivered by fiber optic fiber. The fluorescent light is collected by the objective at the SPCE angle, stripped of the incident light wavelengths by the barrier filter and focused by a tube lens on a surface of EM CCD camera.

FIG. 16 is a schematic (left) and prototype (right) of the SPAM microscope in RK configuration. The excitation light path 12 for RK configurations is shown in red. Sample 14 may be, e.g., a cell (as depicted) that is placed on a light translucent material 16 coated with a thin layer of noble metal (metal layer 18), in this depiction within a solution 15. Incident light produces Surface Plasmons propagating along the surface of the metal. These plasmons couple with the light to excite fluorophore 20. Fluorescent light 20 once again couples with the plasmons to emerge at the bottom of the coverslip at the SPCE angle 22 (which is smaller than SPR angle) as a fluorescent ring 24. The fluorescent ring 24 (or portion thereof) traversed immersion oil (not depicted) and objective 28. The emitted light in the form of a fluorescent ring 24 may then pass a barrier filter 34 and a tube lens 36 before arriving at a light detector 38.

SPAM microscopes may also include one or more of the following alternative arrangements: (1) Improved illumination path. The prototype uses home-made optical fiber to guide the light from a laser to a sample. The final version of SPAM will include 3D manipulator to hold an objective to fill (but not to overfill) the front aperture of the objective. (2) Incorporate the ability to measure rotational motions. Fluorescence coupling to surface plasmons dramatically depends on the orientation of the molecule transition moment, i.e. the method is particularly suited to measurements of protein orientation changes. With SPAM a ~5-fold increase in sensitivity was found based on measurements of rotational motion in comparison with method of polarized fluorescence using TIRF.

Figure 17:
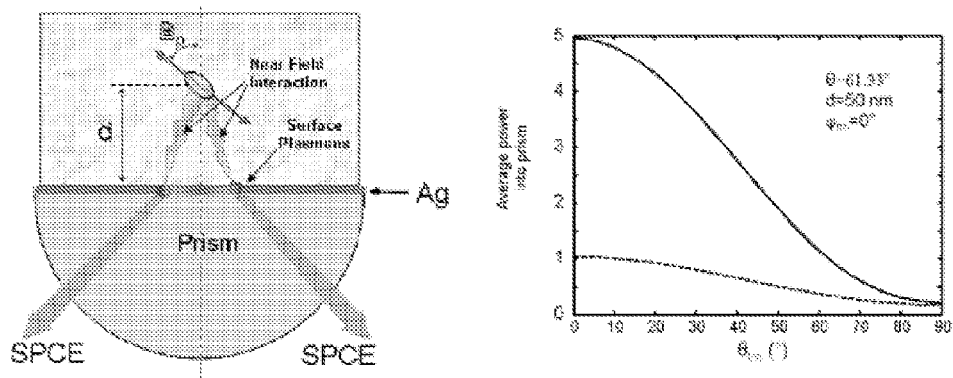
FIG. 17 shows the coupling of fluorescent dipole moments to surface plasmons (left) and comparison of the dependence of the transition moment angle for TIRF and SPAM (right).

A three layer system is shown in FIG. 17 (KR configuration, left). For such system transition moments orthogonal to the metal surface will preferentially couple to surface plasmons and only p-polarized SPCE can be observed. The decay times, the probability that an emitted photon goes into the glass prism, and the percentage of the photons into the glass prism that are p-polarized depend on the fluorophore position and transition moment orientation. The dependence is quantitated in FIG. 17 (right). It is seen that at every value of transition moment dipole angle, SPAM is more sensitive than TIRF. The enhancement is the greatest for vertical orientations of the dipole. The slope for dipole angles 50°±10° is ~5 times greater for the SPAM curve than for TIRF curve, i.e. we can expect ~5-fold larger sensitivity to change in polar angle.

FIG. 17. Coupling of fluorescent dipole moments to surface plasmons (left) and comparison of the dependence of the transition moment angle for TIRF and SPAM (right). To incorporate this design, it is only necessary to insert a polarizing prism (e.g. calcite prism) before the camera. The exciting light is already polarized (both in KR and RK configurations), and calcite prism will measure both orthogonal components of fluorescence.

Figure 18:
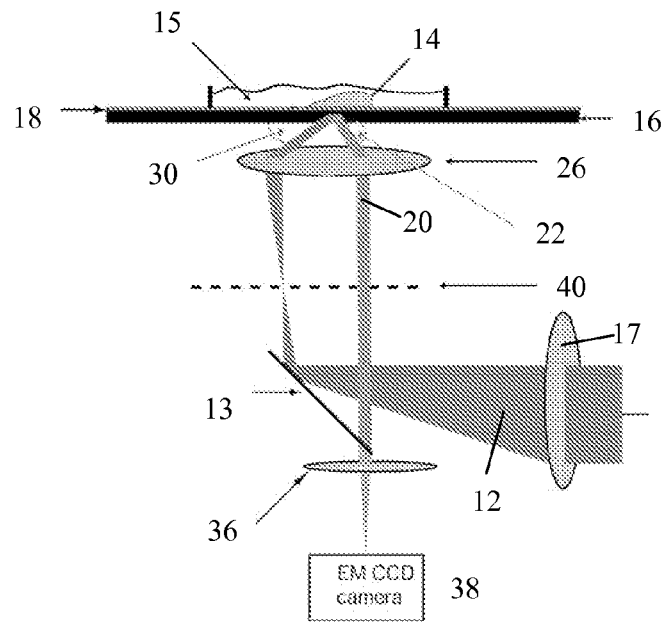
FIG. 18 shows SPAM in Kretschmann configuration.

Kretschmann configuration option. In KR configuration, the sample is illuminated from below; the excitation light has to penetrate the metal layer first. This has the advantage that sample is excited by the evanescent wave, but disadvantage that some light is unable to penetrate the metal layer, in spite of the fact that it is incident on it at theoretically calculated angle. The schematic diagram is shown in FIG. 18. In KR configuration, the excitation light from the expanded Diode Pumped Solid State laser beam (Compass 215M, Coherent, Santa Clara, Calif.) enters the epi-illumination port of the inverted microscope (Olympus IX71). The expanded laser beam, focused at the back focal plane of the objective, is directed by the movable optical fiber adapter to the periphery of the high aperture objective (Olympus 100×, NA=1.65), where it refracts and propagates towards the sapphire-metal/buffer interface.

FIG. 18. SPAM in Kretschmann configuration. A Surface Plasmon Assisted Microscope in Kretschmann configuration is shown. A light beam 12 is incident perpendicularly below sample 14 and may include a beam expander lens 17. Sample 14 may be, e.g., a cell (as depicted) that is placed on a light translucent material 16 coated with a thin metal layer 18, e.g., a noble metal layer. Incident light produces Surface Plasmons propagating along the surface of the metal. These plasmons couple with the light to excite fluorescence from a fluorophore 20. Fluorescent light 20 once again couples with the plasmons to emerge at the bottom of the coverslip at the SPCE angle 22 (which is smaller than SPR angle). The surface plasmon assisted emission strikes objective 28 and traverses tube lens 36 before being detected by a light detector 38 (e.g., a CCD camera, a photomultiplies, a photodiode or even an optical fiber bundle). The far field fluorescence 30 is reflected by the metal layer 18 as is the scattered excitation light 32, thereby eliminating the majority of the background. The back focal plane 40 for the SPAM microscope in Kretschmann configuration is also shown.

As shown in FIG. 18, when the incidence angle is equal to the SPR angle (~61°, see calculation below and FIG. 19), the light is able to penetrate the metal and illuminate a cell. Excitation light produces an evanescent wave on the aqueous side of the interface {Axelrod, 1989 #21} at the surface of a sample. Normally, the evanescent field decays exponentially in the z-dimension with a penetration depth, $d=\lambda 0/(4\pi(n_g^2 \sin^2 \theta - n_w^2)^{1/2})$, where $\lambda_0$ is the wavelength of the incident light, $n_g$ is glass refractive index, and $n_w (=1.33)$ is the refractive index of water. In our case, however, the detection volume is a composition (product) of evanescent wave penetration depth and distance-dependent coupling with surface plasmons. In addition, the detection volume is further reduced by a metal quenching of excited fluorophores at a close proximity (below 10 nm). We showed above that the height of the detected volume is 40-70 nm, depending on the orientation of the excited dipoles. The fluorescent light, emitted at SPCE angle, is collected by the objective. The sample rests on a moveable piezo stage (Nano-H100, Mad City Labs, Madison, Wis.) controlled by a Nano-Drive. This provides sufficient resolution to place the region of interest (ROI) in a position conjugate to the aperture. The fluorescent light is collected through the same objective and projected onto a tube lens, which focuses it at the photosensitive area of the EM CCD camera (Hamamatsu ImagEM).

The calculation of incident angle for KR configuration the angle is shown below. Consider a slab shaped material between the glass and water interfaces. Incident light (TIR Laser) transmits the glass/metal interface, undergoes multiple reflections between the metal/water and glass/metal interfaces, and then emerges as a refracted ray in the water medium. The z=0 field intensities in the water medium of the multilayered system were tabulated as a function of incidence angle $\Theta$. Results (dotted line, FIG. 19) are expressed as intensities for p-polarized incident electric field. Ip.

Figure 19:
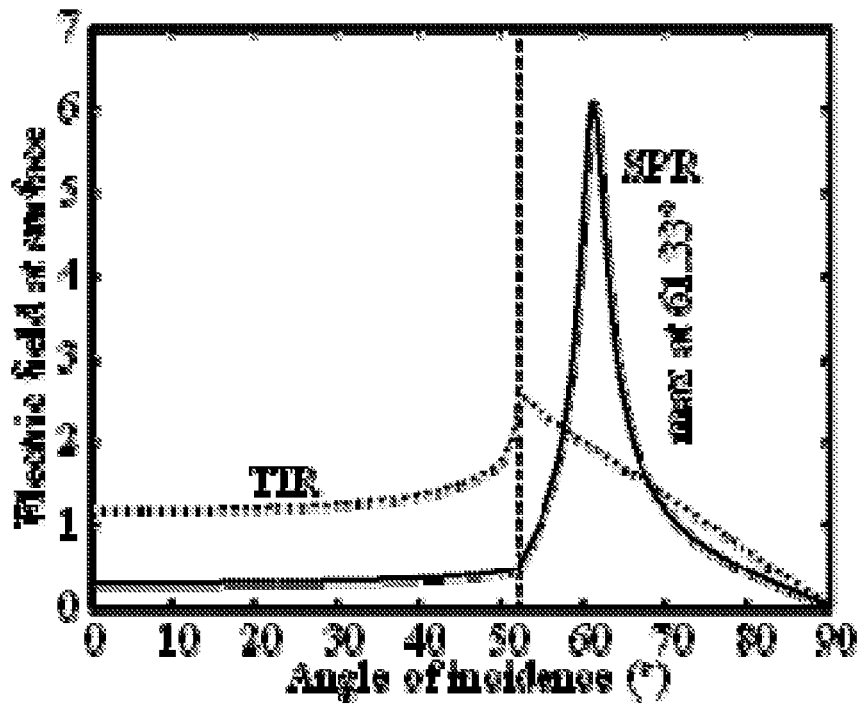
FIG. 19 shows the electric field of the evanescent wave at the surface. It is normalized to the electric field of the incident wave.

FIG. 19 shows the electric field of the evanescent wave at the surface. It is normalized to the electric field of the incident wave. For SPAM it is possible to use a simple dielectric/glass interface and the multilayer electric/silver/glass system ($\in_n = -11.5 + 8.3i$) both for incident light wavelength of 532 nm. The metal (~20 nm for Al, 50 nm for Au or Ag) film is characterized by a complex dielectric constant, $\in_2$. Insertion of the metal film dramatically perturbs the z=0 field intensities in the water medium {Axelrod, 1992 #844; Weber, 1979 #850; Ford, 1984 #851}. The film reflects or absorbs s-polarized incident light permitting negligible light transmission for all incidence angles. Similarly, the film reflects or absorbs p-polarized incident light permitting negligible transmission for almost all angles. However, a dramatic enhancement of transmission occurs in a narrow peak for incidence angle $\Theta_{sp}$ ~61.33° just larger than $\Theta_c$. Angle $\Theta_{sp}$ is the surface plasmon angle where transmission enhancement occurs due to the resonant excitation of electron oscillations (surface plasmons) propagating along the dielectric/metal interface. This phenomenon occurs at interfaces where constituent materials have real dielectric constants with opposite signs.

Intensities in the SPAM experiment are shown as a solid line in FIG. 19 for p-polarized ($I_p$) incident light. Like the evanescent field for p-polarized incident light in the absence of the metal film, polarization is elliptical but approximates linear polarization along the z-axis and intensity decays exponentially in the distance z from the interface. Both polarization and field depth depend on incidence angle. When the excited dipolar probe is near a planar interface of conducting and/or dielectric material the radiated fields are significantly altered. Dipole radiation fields are expanded in plane waves that are reflected and refracted at the interface then summed to give the fields in the presence of the interface. The plane wave expansion method delineates contributions into propagating transverse and non-propagating longitudinal or evanescent plane waves.

The evanescent waves in the absence of the interface form the dipole near-field. Reflection and refraction at the interface converts some of the evanescent waves into detectable propagating transverse plane waves. SPCE is light associated with the emission dipole near-field that is converted into propagating transverse plane waves by the close proximity of the interface. The interface near the dipole radiator also affects total radiated power. Hellen and Axelrod pointed out that for a fluorophore under steady illumination the dissipated power must equal the absorbed power implying that a fixed-power, rather than a fixed-amplitude, dipole radiator is the appropriate model for probe emission near an interface. An important consequence of this model, observed for cells adsorbed to metal coated glass, is that the metal film totally quenches fluorescence from probes within ~10 nm of the interface.

Increase magnification of the objective to avoid undersampling. As mentioned before, the image was undersampled by a factor of 1.8 using the 1.65 NA objective. The situation is even worse for 1.45 objective: the pixel size of the camera is 16 μm×16 μm. For the 60× NA 1.45 objective and 532 nm illumination, the back projected size of the pixel of the camera is 16 μm/60=266 nm, larger than the Rayleigh resolution limit of ~200 nm, and much larger than the Nyquist ideal spatial sampling of 200/2.3≈90 nm. The images are undersampled by a factor of 266/90≈3. While undersampling allows the light to be concentrated on fewer pixels and increases the effective sensitivity of the camera, it limits its spatial resolution. It is proposed to insert (Qioptiq 2×J Clamp SC20).

Figure 20:
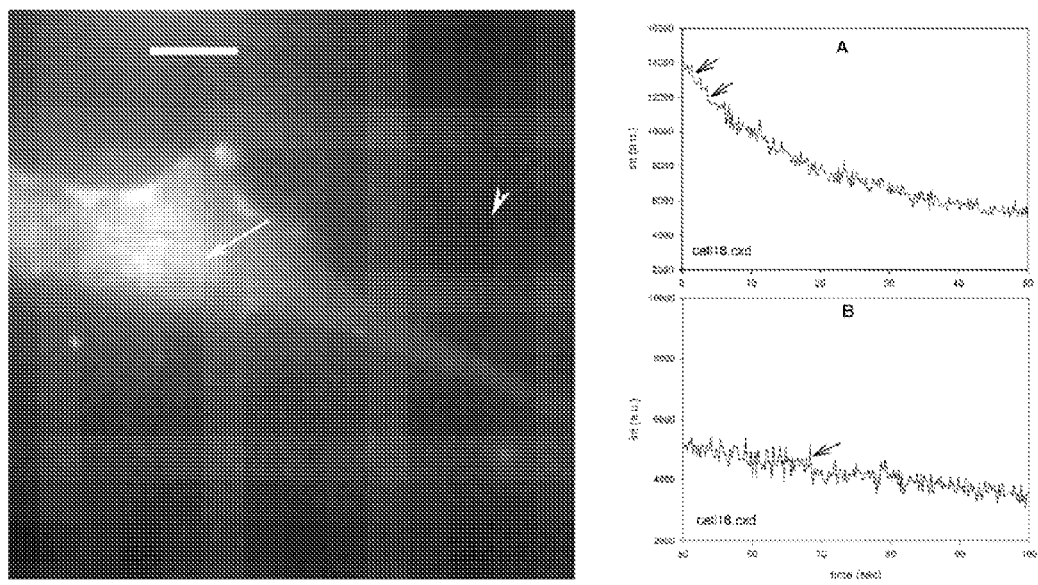
FIG. 20 shows a human neuroblastoma cells on a gold-sapphire coverslip in which presenilin was stained with Alexa488 and viewed by RK using the present invention (FIG. 20, left).

FIG. 20 shows a human neuroblastoma cells on a gold-sapphire coverslip, in which presenilin was stained with Alexa488 and viewed by RK using the present invention (FIG. 20, left). FIG. 20 (right), is a time course of photobleaching of molecule indicated by the arrow (arrowhead is background which was subtracted from signal). Bar is 10 um.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

1. Gryczynski, I.; Malicka, J.; Gryczynski, Z.; Lakowicz, J. R., Surface plasmon-coupled emission: A new method for sensitive fluorescence detection. In Topics in fluorescence, Metal-Enhanced fluorescence, Lakowicz, J.; Geddes, C. D., Eds. Kluwer Academic/Plenum Publishers: 2005; Vol. 8, pp 381-403.
2. Gryczynski, Z.; Gryczynski, I.; Matveeva, E.; Malicka, J.; Nowaczyk, K.; Lakowicz, J. R., Surface-plasmon-coupled emission: new technology for studying molecular processes. Methods Cell Biol 2004, 75, 73-104.
3. Lakowicz, J. R., Radiative decay engineering 3. Surface plasmon-coupled directional emission. Anal Biochem 2004, 324, (2), 153-69.
4. Lakowicz, J. R.; Malicka, J.; Gryczynski, I.; Gryczynski, Z., Directional surface plasmon-coupled emission: A new method for high sensitivity detection. Biochem Biophys Res Commun 2003, 307, (3), 435-9.
5. Calander, N., Theory and simulation of surface plasmon-coupled directional emission from fluorophores at planar structures. Anal Chem 2004, 76, (8), 2168-73.
6. Neogi, A.; Morkoc, H.; Kuroda, T.; Tackeuchi, A., Coupling of spontaneous emission from GaN—AlN quantum dots into silver surface plasmons. Opt Lett 2005, 30, (1), 93-5.
7. Gryczynski, I.; Malicka, J.; Gryczynski, Z.; Lakowicz, J.; Malicka, I., Surface plasmon-coupled emission using gold film. J. Phys. Chem. B 2004, 108, 12568-12574.
8. Gryczynski, I.; Malicka, J.; Gryczynski, Z.; Lakowicz, J. R., Radiative decay engineering 4. Experimental studies of surface plasmon-coupled directional emission. Anal Biochem 2004, 324, (2), 170-82.
9. Malicka, J.; Gryczynski, I.; Fang, J.; Kusba, J.; Lakowicz, J. R., Increased resonance energy transfer between fluorophores bound to DNA in proximity to metallic silver particles. Anal Biochem 2003, 315, (2), 160-9.
10. Malicka, J.; Gryczynski, I.; Gryczynski, Z.; Lakowicz, J. R., Use of surface plasmon-coupled emission to measure DNA hybridization. J Biomol Screen 2004, 9, (3), 208-15.
11. Borejdo, J.; Calander, N. G., Z.; Gryczynski, I., Fluorescence Correlation Spectroscopy in Surface Plasmon Coupled Emission Microscope. Optics Express 2006, 14, (17), 7878-7888.
12. Gryczynski, Z.; Borejdo, J.; Calander, N.; Matveeva, E. G.; Gryczynski, I., Minimization of detection volume by surface-plasmon-coupled emission. Anal Biochem 2006, 356, (1), 125-31.
13. Gryczynski, Z.; Gryczynski, I.; Lakowicz, J. R., Fluorescence-sensing methods. Methods Enzymol 2003, 360, 44-75.

14. Frey, B. L.; Jordan, C. E.; Kornguth, S.; Corn, R. M., Control of the specific adsorption of proteins onto gold surfaces with poly(l-ysine) monolayers. Anal. Chem. 1995, 67, 4452-4457.
15. Frutos, A. G.; Corn, R. M., SPR of ultrathin organic films. Anal. Chem. 1998, 449A-455A.
16. Jordan, C. E.; Frey, B. L.; Kornguth, S.; Corn, R. M., Characterization of Poly-L-lysine adsorption onto alkanethiol-modified gold surfaces with polarization-modulation fourier transform infrared spectroscopy and surface plasmon resonance measurements. Langmuir 1994, 10, 3642-3648.
17. Liedberg, B.; Lundstrom, I., Principles of biosensing with an extended coupling matrix and surface plasmon resonance. Sensors and Actuators B 1993, 11, 63-72.
18. Melendez, J.; Carr, R.; Bartholomew, D. U.; Kukanskis, K.; Elkind, J.; Yee, S.; Furlong, C.; Woodbury, r., A commercial solution for surface plasmon sensing. Sensors and Actuators B 1996, 35-36, 212-216.
19. Salamon, Z.; Macleod, H. A.; Tollin, G., Surface plasmon resonance spectroscopy as a tool for investigating the biochemical and biophysical properties of membrane protein systems. II: Applications to biological systems. Biochim Biophys Acta 1997, 1331, (2), 131-52.
20. Gryczynski, Z.; Matveeva, E.; Calander, N.; Zhang, J.; Lakowicz, J.; Gryczynski, I., Surface Plasmon Coupled Emission—Novel Technology for Studying Thin Layers of BioMolecular Assemblies. In Surface Plasmon Nanophotonics, Brongersma, M. L.; Kik, P. G., Eds. Springer: 2007; pp 247-265.
21. Barnes, W. L., Topical review: Fluorescence near interfaces: the role of photonic mode density. J. Modern Optics 1998, 454, (4), 661-699.
22. Lakowicz, J. R., Radiative decay engineering: biophysical and biomedical applications. Anal Biochem 2001, 298, (1), 1-24.
23. Lakowicz, J. R.; Shen, B.; Gryczynski, Z.; D'Auria, S.; Gryczynski, I., Intrinsic fluorescence from DNA can be enhanced by metallic particles. Biochem Biophys Res Commun 2001, 286, (5), 875-9.
24. Lakowicz, J. R.; Shen, Y.; D'Auria, S.; Malicka, J.; Fang, J.; Gryczynski, Z.; Gryczynski, I., Radiative decay engineering. 2. Effects of Silver Island films on fluorescence intensity, lifetimes, and resonance energy transfer. Anal Biochem 2002, 301, (2), 261-77.
25. Worthing, P. T.; Barnes, W. L., Spontaneous emission within metal-clad microcavities. J. Opt. A. Pure Appl. Opt. 1999, 1, 501-506.
26. Malicka, J.; Gryczynski, I.; Kusba, J.; Lakowicz, J. R., Effects of metallic silver island films on resonance energy transfer between N,N'-(dipropyl)-tetramethyl-indocarbocyanine (Cy3)- and N,N'-(dipropyl)-tetramethyl-indodicarbocyanine (Cy5)-labeled DNA. Biopolymers 2003, 70, (4), 595-603.
27. Borejdo, J.; Gryczynski, Z.; Calander, N.; Muthu, P.; Gryczynski, I., Application of surface plasmon coupled emission to study of muscle. Biophys J 2006, 91, (7), 2626-35.
28. Muthu, P.; Gryczynski, I.; Gryczynski, Z.; Talent, J.; Akopova, I.; Jain, K.; Borejdo, J., Decreasing photobleaching by silver island films: application to muscle. Anal Biochem 2007, 366, (2), 228-36.
29. miRBase::Sequences. http://microrna.sanger.ac.uk/cgi-bin/sequences/browse.pl (Jul. 31, 2007),
30. Gryczynski, I.; Gryczynski, Z.; Lakowicz, J. R., Two-photon excitation by the evanescent wave from total internal reflection. Anal Biochem 1997, 247, (1), 69-76.
31. Lakowicz, J. R.; Gryczynski, Z.; Gryczynski, I., On the possibility of evanescent wave excitation distal from a solid-liquid interface using light quenching. Photochem Photobiol 1996, 64, (4), 636-41.
32. Matveeva, E.; Gryczynski, Z.; Malicka, J.; Gryczynski, I.; Lakowicz, J. R., Metal-enhanced fluorescence immunoassays using total internal reflection and silver island-coated surfaces. Anal Biochem 2004, 334, (2), 303-11.
33. Enderlein, J.; Robbinson, D. L.; Ambrose, W. P.; Keller, R. A., Molecular shot noice, burst size distribution, and single-molecule detection in fluid flow. Effect of multiple occupancy. J. Phys. Chem. A 1998, 102, 6089.
34. Erdman, R.; Enderlein, J.; Siedel, C., Single molecule detection and ultrasensitive analysis in the life science. Cytometry 1999, 36, (3), 161-164.

What is claimed is:

1. A surface plasmon assisted microscope (10) system capable of detecting single molecules, the microscope system comprising:
a light translucent material (16);
a metal layer (18) disposed on the light translucent material (16), wherein the thickness of the metal layer (18) is 50 nM or less, wherein the metal layer (18) is gold, silver, aluminum or copper or combinations thereof;
a medium (15) disposed on the metal layer (18), the medium (15) comprising one or more fluorophores capable of binding a target analyte;
a microscope positioned to observe the emission from the one or more fluorophores in the medium;
an excitation source capable of exciting the one or more fluorophores, the excitation source positioned to strike the light translucent material (16) at a first angle; and
a light detector (38) that detects emitted light (20) generated by excited fluorophores at a second angle, wherein light (20) emitted by the one or more fluorophores at the surface plasmon angle (22) is detected through the microscope (10), wherein the light detector (38) and the excitation source are located on opposite sides of the metal layer (18), such that single molecules may be detected without significantly degrading fluorophore emissions.

2. The microscope of claim 1, wherein the metal is deposited onto the light translucent material by vapor deposition, electroless plating, chemical vapor deposition, or photoreduction.

3. The microscope of claim 1, wherein the light translucent material (16) comprises glass, silica, a polymer, quartz, plastic, borosilicate glass and combinations thereof.

4. The microscope of claim 1, wherein the excitation source is arranged to direct light comprising an excitation wavelength through the light translucent material and then to the metal layer such that the angle of incidence on the first layer is equal to the surface plasmon angle of said excitation wavelength.

5. The microscope of claim 1, wherein the microscope (10) comprises a high numerical aperture (NA) objective.

6. The microscope of claim 1, wherein the target comprises a molecule within a cell.

7. The microscope of claim 1, wherein the detector (38) selectively detects light emissions from within a cell.

8. The microscope of claim 1, wherein the detection of the one or more fluorophores is from fluorophores that are within 50 nM from the metal surface.

9. The microscope of claim 1, wherein the light detector (38) detects light emissions over time and stores the images.

10. The microscope of claim 1, wherein the fluorophores (20) are selected from 7-Amino-actinomycin D; Acridine orange; Acridine yellow; Alexa Fluor; AnaSpec; Auramine O; Auramine-rhodamine stain; Benzanthrone; 9,10-Bis(phenylethynyl)anthracene; 5,12-Bis(phenylethynyl)naphthacene; CFDA-SE; CFSE; Calcein; Carboxyfluorescein; 1-Chloro-9,10-bis(phenylethynyl)anthracene; 2-Chloro-9,10-bis(phenylethynyl)anthracene; Coumarin; Cyanine; DAPI; Dark quencher; Dioc6; DyLight Fluor; Ethidium bromide; Fluorescein; Fura-2; Fura-2-acetoxymethyl ester; Green fluorescent protein; Hilyte Fluor; Hoechst stain; Indian yellow; Luciferin; Perylene; Phycobilin; Phycoerythrin; Phycoerythrobilin; Propidium iodide; Pyranine; Rhodamine; RiboGreen; Rubrene; Ruthenium(II) tris(bathophenanthroline disulfonate); SYBR Green; Stilbene; TSQ; Texas Red; Umbelliferone and Yellow fluorescent protein.

11. A surface plasmon assisted microscope (10) system capable of detecting single molecules, the microscope system comprising:
  a light translucent material (16);
  a metal layer (18) disposed on the light translucent material (16), wherein the thickness of the metal layer (18) is 50 nM or less;
  a medium (15) disposed on the metal layer (18), the medium (15) comprising one or more fluorophores (20) capable of binding a target analyte in a sample (14);
  an excitation source positioned to traverse a microscope (10) objective into the light translucent material (16) and striking the metal layer (18), wherein surface plasmons created by the combination of exciting the one or more fluorophores (20) in the sample (14) are amplified at the metal layer (18), wherein the light strikes the light translucent material (16) at a first angle;
  a light microscope positioned to capture the emission from the one or more fluorophores (20) in the medium at a second angle; and
  a light detector (38) positioned to selectively detect emitted light generated by excited fluorophores (20) that are amplified by the surface plasmons, wherein the light detector (38) and the excitation source are located on opposite sides of the metal layer (18), such that single molecules may be detected.

12. The microscope of claim 11, wherein the metal layer (18) comprises silver, gold, aluminum, or copper or combinations thereof.

13. The microscope of claim 11, wherein the metal is deposited onto the light translucent material by vapor deposition, electroless plating, chemical vapor deposition, or photoreduction.

14. The microscope of claim 11, wherein the light translucent material comprises glass, silica, a polymer, quartz, plastic, borosilicate glass and combinations thereof.

15. The microscope of claim 11, wherein the excitation source is arranged to direct light comprising an excitation wavelength through the light translucent material (16) to strike the metal layer (18) such that the angle of incidence on the first layer is equal to the surface plasmon angle of the excitation wavelength.

16. The microscope of claim 11, wherein the microscope comprises a high numerical aperture (NA) objective.

17. The microscope of claim 11, wherein the sample (14) comprises a molecule within a cell.

18. The microscope of claim 11, wherein the light detector (38) selectively detects light emissions from within a cell.

19. The microscope of claim 11, wherein the light detection (38) of the one or more fluorophores is from fluorophores within 50 nM from the metal surface.

20. The microscope of claim 11, wherein the light detector (38) detects light emissions over time and stores the images.

21. The microscope of claim 11, wherein the fluorophores comprise one or more fluorophores (20) that bind to one or more different target molecules concurrently, wherein the fluorophores (20) are selected from 7-Amino-actinomycin D; Acridine orange; Acridine yellow; Alexa Fluor; AnaSpec; Auramine O; Auramine-rhodamine stain; Benzanthrone; 9,10-Bis(phenylethynyl)anthracene; 5,12-Bis(phenylethynyl)naphthacene; CFDA-SE; CFSE; Calcein; Carboxyfluorescein; 1-Chloro-9,10-bis(phenylethynyl)anthracene; 2-Chloro-9,10-bis(phenylethynyl)anthracene; Coumarin; Cyanine; DAPI; Dark quencher; Dioc6; DyLight Fluor; Ethidium bromide; Fluorescein; Fura-2; Fura-2-acetoxymethyl ester; Green fluorescent protein; Hilyte Fluor; Hoechst stain; Indian yellow; Luciferin; Perylene; Phycobilin; Phycoerythrin; Phycoerythrobilin; Propidium iodide; Pyranine; Rhodamine; RiboGreen; Rubrene; Ruthenium(II) tris(bathophenanthroline disulfonate); SYBR Green; Stilbene; TSQ; Texas Red; Umbelliferone and Yellow fluorescent protein.

22. A method for detecting fluorescence using surface plasmon-coupled emission with a microscope, comprising:
  positioning a light translucent material (16) onto which a metal layer (18) capable of surface plasmon amplification has been formed in a light path (12);
  binding an analyte to one or more fluorophores in a sample (14) on the surface of a metal layer (18), wherein the fluorophores are within 50 nanometers of the surface;
  striking the analyte and the one or more types of fluorophores (20) with a coherent light at a first angle, wherein the combination of fluorescence emission and the surface plasmons emit light at a second angle (22); and
  detecting the light emitted at the second angle, wherein light emitted by the one or more fluorophores (20) at the second angle is detected through the microscope, wherein the emitted light is detected at a location that is on a side of the metal layer (18) that is opposite to the side of the metal layer (18) that is adjacent to a source of the Cohen rent light, such that the analyte may be detected without significantly degrading fluorophore (20) emissions.

23. The method of claim 22, wherein the microscope and the light source are positioned in a Reverse Kretschmann configuration.

24. The method of claim 22, wherein the microscope and the light source are positioned in a Kretschmann configuration.

25. The method of claim 22, wherein the analyte comprise at least one of antibodies, fragments of an antibodies, peptides, antigens, nucleic acids, polypeptides, lipids, carbohydrates, polysaccharides, minerals, vitamins, cells and tissues.

26. The method of claim 22, wherein the analyte is bound to the one or more fluorophores (20).

27. The method of claim 22, wherein the metal is deposited on the light translucent material (16) by vapor deposition, electroless plating, chemical vapor deposition, or photoreduction.

28. The method of claim 22, wherein the metal comprises aluminum, silver, gold, copper and combinations thereof.

29. The method of claim 22, wherein the light translucent material (16) comprises glass, silica, a polymer, quartz, plastic, borosilicate glass and combinations thereof.

30. The method of claim 22, wherein analyte is detected without significantly degrading fluorophore (20) emissions, wherein the fluorophores (20) are selected from 7-Amino-actinomycin D; Acridine orange; Acridine yellow; Alexa Fluor; AnaSpec; Auramine O; Auramine-rhodamine stain; Benzanthrone; 9,10-Bis(phenylethynyl)anthracene; 5,12-Bis(phenylethynyl)naphthacene; CFDA-SE; CFSE; Calcein;

Carboxyfluorescein; 1-Chloro-9,10-bis(phenylethynyl)anthracene; 2-Chloro-9,10-bis(phenylethynyl)anthracene; Coumarin; Cyanine; DAPI; Dark quencher; Dioc6; DyLight Fluor; Ethidium bromide; Fluorescein; Fura-2; Fura-2-acetoxymethyl ester; Green fluorescent protein; Hilyte Fluor; Hoechst stain; Indian yellow; Luciferin; Perylene; Phycobilin; Phycoerythrin; Phycoerythrobilin; Propidium iodide; Pyranine; Rhodamine; RiboGreen; Rubrene; Ruthenium(II) tris(bathophenanthroline disulfonate); SYBR Green; Stilbene; TSQ; Texas Red; Umbelliferone and Yellow fluorescent protein.

31. A method for detecting fluorescence of single molecules using surface plasmon-coupled emission without degrading fluorophore (20) emissions with a microscope, comprising:
positioning a light translucent material (16) onto which a metal layer (18) capable of surface plasmon amplification has been formed in a light path (12);
binding an analyte to one or more fluorophores (20) in a sample (14) that is disposed on the surface of the metal layer (18), wherein the fluorophores are within 50 nanometers of the metal surface, wherein the metal layer (18) is gold, silver, aluminum or copper or combinations thereof;
striking the analyte and the one or more types of fluorophores (20) with the light at a first angle, wherein the combination of fluorescence emission and the surface plasmons emit light at a second angle (22) and the metal layer (18) forms a mirror that reflects background emissions that are non-specific and farther than 50 nanometers from the metal surface; and
detecting the light emitted at the second angle (22), wherein light emitted by the one or more fluorophores (20) at the second angle is detected through the microscope, wherein the emitted light is detected at a location that is on a side of the metal layer (18) that is opposite to the side of the metal layer (18) that is adjacent to a source of the light, such that the analyte may be detected without significantly degrading fluorophore (20) emissions.

32. The method of claim 31, wherein the microscope and the light source are positioned in a Reverse Kretschmann configuration.

33. The method of claim 31, wherein the analyte comprise at least one of antibodies, fragments of an antibodies, peptides, antigens, nucleic acids, polypeptides, lipids, carbohydrates, polysaccharides, minerals, vitamins, cells and tissues.

34. The method of claim 31, wherein the analyte is bound to the one or more fluorophores, wherein the fluorophores (20) are selected from 7-Amino-actinomycin D; Acridine orange; Acridine yellow; Alexa Fluor; AnaSpec; Auramine O; Auramine-rhodamine stain; Benzanthrone; 9,10-Bis(phenylethynyl)anthracene; 5,12-Bis(phenylethynyl)naphthacene; CFDA-SE; CFSE; Calcein; Carboxyfluorescein; 1-Chloro-9,10-bis(phenylethynyl)anthracene; 2-Chloro-9,10-bis(phenylethynyl)anthracene; Coumarin; Cyanine; DAPI; Dark quencher; Dioc6; DyLight Fluor; Ethidium bromide; Fluorescein; Fura-2; Fura-2-acetoxymethyl ester; Green fluorescent protein; Hilyte Fluor; Hoechst stain; Indian yellow; Luciferin; Perylene; Phycobilin; Phycoerythrin; Phycoerythrobilin; Propidium iodide; Pyranine; Rhodamine; RiboGreen; Rubrene; Ruthenium(II) tris(bathophenanthroline disulfonate); SYBR Green; Stilbene; TSQ; Texas Red; Umbelliferone and Yellow fluorescent protein.

35. The method of claim 31, wherein the metal is deposited on the translucent material by vapor deposition, electroless plating, chemical vapor deposition, or photoreduction.

36. The method of claim 31, wherein the translucent material (16) comprises glass, silica, a polymer, quartz, plastic, borosilicate glass and combinations thereof.

* * * * *

UNITED STATES PATENT AND TRADEMARK OFFICE
CERTIFICATE OF CORRECTION

PATENT NO. : 7,956,989 B2
APPLICATION NO. : 12/018107
DATED : June 7, 2011
INVENTOR(S) : Gryczynski et al.

Page 1 of 1

It is certified that error appears in the above-identified patent and that said Letters Patent is hereby corrected as shown below:

Col. 1, line 37
Replace "illumination system, teaches" with --illumination system, and teaches--

Col. 1, lines 56-57
Replace "teaches a single molecule" with --teaches single molecule--

Col. 2, line 4
Replace "microscope has a specimen holding" with --microscope having a specimen holding--

Col. 3, line 7
Replace "amplified the surface plasmons," with --amplified by the surface plasmons,--

Col. 4, line 2
Replace "observation; d-KR excitation" with --observation; FIG. 2d-KR excitation--

Col. 10, line 52
Replace "before, it results from that does not" with --before, that it does not--

Col. 11, line 7
Replace "observation; d-KR" with --observation; FIG. 2d-KR--

Col. 24, line 47
Replace "fragments of an antibodies" with --fragments of an antibody--

Col. 26, line 9
Replace "fragments of an antibodies" with --fragments of an antibody--

Signed and Sealed this
Twentieth Day of September, 2011

David J. Kappos
*Director of the United States Patent and Trademark Office*